United States Patent
Goldberg et al.

(10) Patent No.: US 9,814,536 B2
(45) Date of Patent: Nov. 14, 2017

(54) METHODS AND SYSTEMS FOR ASSIGNING INPUT DEVICES TO TELEOPERATED SURGICAL INSTRUMENT FUNCTIONS

(71) Applicant: INTUITIVE SURGICAL OPERATIONS, INC., Sunnyvale, CA (US)

(72) Inventors: Randal P Goldberg, Campbell, CA (US); Michael Hanuschik, Mountain View, CA (US); Paul Millman, San Jose, CA (US); Paul W. Mohr, Mountain View, CA (US); Thomas R. Nixon, San Jose, CA (US); David Robinson, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/072,303

(22) Filed: Mar. 16, 2016

(65) Prior Publication Data
US 2016/0192998 A1 Jul. 7, 2016

Related U.S. Application Data

(63) Continuation of application No. 14/028,006, filed on Sep. 16, 2013, now Pat. No. 9,301,811.
(Continued)

(51) Int. Cl.
*A61B 19/00* (2006.01)
*A61B 34/35* (2016.01)
(Continued)

(52) U.S. Cl.
CPC .............. *A61B 34/35* (2016.02); *A61B 18/00* (2013.01); *A61B 34/30* (2016.02); *A61B 34/37* (2016.02);
(Continued)

(58) Field of Classification Search
CPC ......... A61B 34/35; A61B 18/00; A61B 90/98; A61B 34/74; A61B 34/37; A61B 34/30;
(Continued)

(56) References Cited

U.S. PATENT DOCUMENTS 5,991,355 A   11/1999 Dahlke
6,040,537 A   3/2000 McClintock
(Continued)

FOREIGN PATENT DOCUMENTS

CN   1243690 A   2/2000
CN   101297760 A   11/2008
(Continued)

OTHER PUBLICATIONS

Extended European Search Report for Application No. 13851407.0, dated Sep. 9, 2016, 13 pages.
(Continued)

*Primary Examiner* — Jason Holloway
(74) *Attorney, Agent, or Firm* — Jones Robb, PLLC

(57) ABSTRACT

A method of assigning an auxiliary input device to control a surgical instrument in a robotic surgical system may include detecting a first surgical instrument coupled to a first manipulator interface assembly of a teleoperated surgical system, the manipulator interface assembly being controlled by a first input device; detecting which one of a user's left and right hands operates the first input device; and assigning control of an auxiliary function of the first surgical instrument to a first auxiliary input device disposed in a left position relative to a second auxiliary input device if the user's left hand is detected to operate the first input device, or assigning control of an auxiliary function of the first surgical instrument to a second auxiliary input device disposed in a right position relative to the first auxiliary input device if the user's right hand is detected to operate the first
(Continued)

input device. A frame of reference of the left position and right position is relative to a user operating the first input device.

20 Claims, 9 Drawing Sheets

Related U.S. Application Data

(60) Provisional application No. 61/702,166, filed on Sep. 17, 2012.

(51) Int. Cl.
| | |
|---|---|
| A61B 34/30 | (2016.01) |
| A61B 34/37 | (2016.01) |
| A61B 90/98 | (2016.01) |
| A61B 18/00 | (2006.01) |
| A61B 18/14 | (2006.01) |
| A61B 17/00 | (2006.01) |
| A61B 34/00 | (2016.01) |

(52) U.S. Cl.
CPC ............ *A61B 34/74* (2016.02); *A61B 90/98* (2016.02); *A61B 18/14* (2013.01); *A61B 34/25* (2016.02); *A61B 2017/00225* (2013.01); *A61B 2017/00973* (2013.01); *A61B 2034/254* (2016.02); *G05B 2219/40195* (2013.01)

(58) Field of Classification Search
CPC ......... A61B 2017/00225; A61B 34/25; A61B 2034/254; A61B 2017/00973; A61B 18/14; G05B 2219/40195
See application file for complete search history.

(56) References Cited

U.S. PATENT DOCUMENTS

| | | | |
|---|---|---|---|
| 6,074,388 | A | 6/2000 | Tockweiler et al. |
| 6,113,596 | A | 9/2000 | Hooven et al. |
| 6,237,604 | B1 | 5/2001 | Burnside et al. |
| 6,493,608 | B1 | 12/2002 | Niemeyer |
| 6,522,906 | B1 | 2/2003 | Salisbury, Jr. et al. |
| 6,840,938 | B1 | 1/2005 | Morley et al. |
| 6,849,071 | B2 | 2/2005 | Whitman et al. |
| 6,994,708 | B2 | 2/2006 | Manzo |
| D517,501 | S | 3/2006 | Kotyk |
| 7,122,032 | B2 | 10/2006 | Shinmura et al. |
| 7,217,269 | B2 | 5/2007 | El-Galley et al. |
| 7,320,700 | B2 | 1/2008 | Cooper et al. |
| 7,353,068 | B2 | 4/2008 | Tanaka et al. |
| 7,367,973 | B2 | 5/2008 | Manzo et al. |
| 7,379,563 | B2 | 5/2008 | Shamaie |
| 7,428,439 | B1 | 9/2008 | Reynolds et al. |
| 7,594,912 | B2 | 9/2009 | Cooper et al. |
| 8,120,301 | B2 | 2/2012 | Goldberg et al. |
| 8,398,541 | B2 | 3/2013 | DiMaio et al. |
| 8,398,634 | B2 | 3/2013 | Scott et al. |
| 8,418,073 | B2 | 4/2013 | Mohr et al. |
| 8,423,182 | B2 | 4/2013 | Robinson et al. |
| 8,508,173 | B2 | 8/2013 | Goldberg et al. |
| 8,657,808 | B2 | 2/2014 | McPherson et al. |
| 8,862,268 | B2 | 10/2014 | Robinson et al. |
| 9,259,283 | B2* | 2/2016 | Ogawa ............... A61B 19/2203 |
| 9,301,811 | B2 | 4/2016 | Goldberg et al. |
| 9,375,288 | B2 | 6/2016 | Robinson et al. |
| 2002/0152015 | A1 | 10/2002 | Seto |
| 2002/0173799 | A1 | 11/2002 | Besharim et al. |
| 2003/0135204 | A1 | 7/2003 | Lee et al. |
| 2004/0167515 | A1 | 8/2004 | Petersen et al. |
| 2005/0008043 | A1 | 1/2005 | Kousek et al. |
| 2005/0021021 | A1 | 1/2005 | Foltz et al. |
| 2005/0080403 | A1 | 4/2005 | Takahashi |
| 2005/0251156 | A1 | 11/2005 | Toth et al. |
| 2005/0251228 | A1 | 11/2005 | Hamel |
| 2006/0079889 | A1 | 4/2006 | Scott et al. |
| 2006/0087746 | A1 | 4/2006 | Lipow |
| 2006/0142657 | A1 | 6/2006 | Quaid et al. |
| 2006/0271260 | A1 | 11/2006 | Matsuzaki et al. |
| 2007/0005045 | A1 | 1/2007 | Mintz et al. |
| 2007/0013336 | A1 | 1/2007 | Nowlin et al. |
| 2007/0016174 | A1 | 1/2007 | Millman et al. |
| 2007/0078539 | A1 | 4/2007 | Kuhner |
| 2007/0167968 | A1 | 7/2007 | Pandey |
| 2007/0239172 | A1 | 10/2007 | Lee et al. |
| 2008/0020714 | A1 | 1/2008 | Mezhinsky et al. |
| 2008/0046122 | A1 | 2/2008 | Manzo et al. |
| 2008/0125794 | A1 | 5/2008 | Brock et al. |
| 2008/0140158 | A1 | 6/2008 | Hamel et al. |
| 2008/0147089 | A1 | 6/2008 | Loh et al. |
| 2008/0183189 | A1 | 7/2008 | Teichman et al. |
| 2008/0217564 | A1 | 9/2008 | Beyar et al. |
| 2008/0221473 | A1 | 9/2008 | Calancie et al. |
| 2008/0249547 | A1 | 10/2008 | Dunn |
| 2008/0262538 | A1 | 10/2008 | Danitz et al. |
| 2008/0319313 | A1 | 12/2008 | Boivin et al. |
| 2009/0009492 | A1 | 1/2009 | Gregorio et al. |
| 2009/0012533 | A1 | 1/2009 | Barbagli |
| 2009/0024142 | A1 | 1/2009 | Ruiz |
| 2009/0088634 | A1 | 4/2009 | Zhao et al. |
| 2009/0088774 | A1 | 4/2009 | Swarup et al. |
| 2009/0248041 | A1 | 10/2009 | Williams et al. |
| 2009/0275940 | A1 | 11/2009 | Malackowski et al. |
| 2010/0082039 | A1 | 4/2010 | Mohr et al. |
| 2010/0191088 | A1 | 7/2010 | Anderson et al. |
| 2010/0228249 | A1* | 9/2010 | Mohr ................. A61B 1/00009 606/41 |
| 2010/0234857 | A1* | 9/2010 | Itkowitz ............... G09B 23/285 606/130 |
| 2010/0305427 | A1 | 12/2010 | Huber et al. |
| 2011/0045680 | A1 | 2/2011 | Beller et al. |
| 2011/0079626 | A1 | 4/2011 | Viola et al. |
| 2011/0118752 | A1 | 5/2011 | Itkowitz et al. |
| 2011/0118753 | A1 | 5/2011 | Itkowitz et al. |
| 2011/0238079 | A1 | 9/2011 | Hannaford et al. |
| 2011/0276058 | A1 | 11/2011 | Choi et al. |
| 2011/0282140 | A1 | 11/2011 | Itkowitz et al. |
| 2011/0282141 | A1 | 11/2011 | Itkowitz et al. |
| 2012/0046659 | A1 | 2/2012 | Mueller |
| 2012/0071891 | A1 | 3/2012 | Itkowitz et al. |
| 2012/0071892 | A1 | 3/2012 | Itkowitz et al. |
| 2012/0202388 | A1 | 8/2012 | Selig et al. |
| 2012/0310241 | A1 | 12/2012 | Orszulak |
| 2013/0053840 | A1 | 2/2013 | Krapohl et al. |
| 2013/0274734 | A1 | 10/2013 | Maass et al. |
| 2013/0304256 | A1* | 11/2013 | Moll .................. A61B 19/2203 700/247 |
| 2014/0114481 | A1* | 4/2014 | Ogawa ............... A61B 19/2203 700/257 |
| 2014/0128885 | A1 | 5/2014 | Dachs, II et al. |
| 2014/0128886 | A1 | 5/2014 | Holop et al. |
| 2014/0142591 | A1 | 5/2014 | Alvarez et al. |
| 2014/0180272 | A1 | 6/2014 | Dachs, II et al. |
| 2015/0012134 | A1 | 1/2015 | Robinson et al. |

FOREIGN PATENT DOCUMENTS

| | | |
|---|---|---|
| JP | H07308321 A | 11/1995 |
| WO | WO-9749340 A1 | 12/1997 |
| WO | WO-2008098085 A2 | 8/2008 |
| WO | WO-2010008126 A1 | 1/2010 |
| WO | WO-2010104753 A1 | 9/2010 |
| WO | WO-2011060139 A2 | 5/2011 |
| WO | WO-2011125007 A1 | 10/2011 |

OTHER PUBLICATIONS 802.3af-2003—IEEE Standard for Information Technology—Telecommunications and Information Exchange Between Systems—Local and Metropolitan Area Networks—Specific Requirements

(56) References Cited

OTHER PUBLICATIONS

[online], 2003, Current Version Jul. 22, 2003, DOI 10.1109/IEEESTD 2003.94284, Persistent Link: http://ieeexplore.ieee.org/servlet/opac?punumber=8612.
Applied Surgical, Data Sheet for Gemini Operating Room, 1 Page, 2006; Internet: http://appliedsurgicalsolutions.com/.
Dugan, Kelli M., "Stepping Out," Birmingham Business Journal, Mar. 24, 2006, 2 pages; Internet: http://www.oadi.org/client%20news/Applied%20Surgical%20032406.pdf.
Erickson, J.R. et al., "Connectors Take on a new Life," Published Online on Sep. 1, 2012, <URL: http://www.designworlddonline.com/connectors-take-on-a-new-life/>.
Extended European Search Report for Application No. 13836661.2, dated Apr. 28, 2016, 11 pages.
Harris, William, "How Haptic Technology Works," downloaded Oct. 24, 2008, 6 pages; Internet: http://electronics.howstuffworks.com/gadgets/other-gadgets/haptic-technology4.htm.
International Search Report and Written Opinion for Application No. PCT/US2013/059938, dated Dec. 10, 2013, 11 pages.
International Search Report and Written Opinion for Application No. PCT/US2013/068059, dated Feb. 11, 2014, 18 pages.
Linemaster Switch Corp., Brochure titled "Precision Begins with a Linemaster Switch," 8 pages, 2000.
Linemaster Switch Corp., Data Sheet for Linemaster Wireless Linear Foot Switch, Lit-002 Rev D, 2 pages, downloaded Jan. 2, 2009; Internet: http://www.linemaster.com/media/DataSheets/LIT-002%20Rev%20Dsm.pdf.
Linemaster Switch Corp., Information sheet for Linemaster Infrared Wireless Linear Foot Switch, 2 pages, downloaded Jan. 2, 2009; Internet: http://www.linemaster.com/wirelesslinear.shtml.
Medical Design Magazine, "Wireless Footswitch Controls Several Surgical Devices," Nov. 1, 2006, 1 page; Internet: http://medicaldesign.com/engineering-prototyping/wireless_footswitch_controls/index.html.
Partial Supplementary European Search Report for Application No. 13851407.0, dated May 23, 2016, 9 pages.
PCT/US10/26307 International Search Report and Written Opinion of the International Searching Authority, dated Jul. 22, 2010, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wikipedia, entry on "Ergonomics," printed Feb. 24, 2009 at 11:24 p.m., 10 pages; Internet: http://en.wikipedia.org/wiki/Ergonomics.
Office Action dated Oct. 8, 2016 for Chinese Application No. 201380048070.8 filed Sep. 16, 2013, 15 pages.

* cited by examiner

METHODS AND SYSTEMS FOR ASSIGNING INPUT DEVICES TO TELEOPERATED SURGICAL INSTRUMENT FUNCTIONS

CROSS-REFERENCE TO RELATED APPLICATIONS

This application is a continuation of U.S. patent application Ser. No. 14/028,006, filed on Sep. 16, 2013, which claims the benefit of U.S. Provisional Application No. 61/702,166, filed Sep. 17, 2012, the entire contents of each of which is incorporated by reference herein in its entirety.

TECHNICAL FIELD

Aspects of the present disclosure relate to methods and systems for assigning control over surgical instruments from input devices that remotely control a function of the surgical instruments. More particularly, aspects of the present disclosure relate to such methods and systems used in teleoperated (robotic) surgical systems wherein input devices at a surgeon console are assigned to control one or more functions of surgical instruments at a patient side cart.

INTRODUCTION

Some minimally invasive surgical techniques are performed remotely through the use of teleoperated (robotically-controlled) surgical instruments. In such surgical systems, surgeons manipulate input devices at a surgeon console, and those inputs are passed to a patient side cart that interfaces with one or more surgical instruments through various manipulator interface mechanisms. Based on the surgeon's inputs at the surgeon console, the one or more surgical instruments are actuated at the patient side cart to operate on the patient, thereby creating a master-slave control relationship between the surgeon console and the surgical instrument(s) at the patient side cart. The input devices provided at the surgeon console may include, for example, handheld gripping mechanisms that are grasped by the surgeon and used to position and actuate the instrument to perform a desired medical procedure.

In addition to being coupled to various manipulator interface mechanisms at the patient side cart to position and otherwise manipulate the instruments based on manipulation of master inputs at the surgeon console, teleoperated surgical instruments also can perform other auxiliary surgical functions in addition to those under the direct control of the master input devices. By way of example, the surgical instruments may perform various auxiliary functions, such as monopolar or bipolar energy supply (e.g., cautery), suction, irrigation, stapling, clamping, cutting, imaging, etc. As with movement of the instrument in general, the auxiliary surgical functions performed by the surgical instrument are controlled by an input device generally provided at the surgeon console. Such input devices may include, for example, foot pedals that are depressed to send a command to perform the auxiliary function. Auxiliary function input devices also may be operably coupled to manual minimally invasive surgical instruments. For example, a foot pedal may be used to provide control over an auxiliary function, such as, for example, cautery energy delivery, to a manual instrument via an energy generator.

Some surgical systems, whether manual or robotic, pre-assign auxiliary functions to individual auxiliary input devices, e.g., foot pedals. When a specific auxiliary function, e.g., energy supply, is to be implemented by a surgical instrument having a corresponding functional capability, the user can actuate the auxiliary input device assigned to the specific auxiliary function. For example, if a user wishes to supply cautery energy to a surgical instrument that delivers bipolar cautery energy (e.g., as opposed to monopolar energy), the user would provide input at an auxiliary input device (e.g., press a foot pedal) that has been assigned and is logically coupled to provide a bipolar energy delivery command to activate the bipolar energy instrument; likewise with a monopolar energy instrument/monopolar energy-assigned input device.

Various surgical instruments may be added or removed from a robotic surgical system patient side cart depending on the type of surgical procedure desired to be performed. Further, multiple surgical instruments, which may be of similar or different types as the others so mounted, may be used together in performing a surgical procedure. There may be a benefit to provide a teleoperated (robotic) surgical system that dynamically and in an automated manner assigns control over auxiliary functions to auxiliary input devices based on the functional capabilities of the surgical instruments currently being controlled by the user. There may further exist a need to provide an alternative and intuitive manner in which to assign auxiliary input devices to control auxiliary surgical instrument functions in surgical systems, including in teleoperated (robotic) surgical systems.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a method of assigning an auxiliary input device to a surgical instrument in a surgical system can include automatically assigning the auxiliary input device to control an auxiliary function of the surgical instrument based on a position of the auxiliary input device and which of a user's hands is operating another input device operably coupled to control movement of the surgical instrument.

In accordance with another exemplary embodiment, a system for controlling a surgical instrument may include an input device of a surgical system that is operably coupled to generate and transmit an input control signal to control movement of a surgical instrument operably coupled to the surgical system. The system may further include an auxiliary input device and a control system operably coupling the auxiliary input device to control the surgical instrument based on a position of the auxiliary input device and which of a user's hands is operating the input device.

In accordance with yet another exemplary embodiment, a method of assigning an auxiliary input device to control a surgical instrument in a surgical system may include detecting a first surgical instrument coupled to a first manipulator interface assembly of a surgical system, the manipulator interface assembly being controlled by a first input device and detecting which one of a user's left and right hands operates the first input device. The method may further include assigning control of an auxiliary function of the first surgical instrument to a first auxiliary input device disposed in a left position relative to a second auxiliary input device if the user's left hand is detected to operate the first input device or assigning control of an auxiliary function of the first surgical instrument to a second auxiliary input device disposed in a right position relative to the first auxiliary input device if the user's right hand is detected to operate the first input device. A frame of reference of the left position and right position can be relative to a user operating the first input device.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
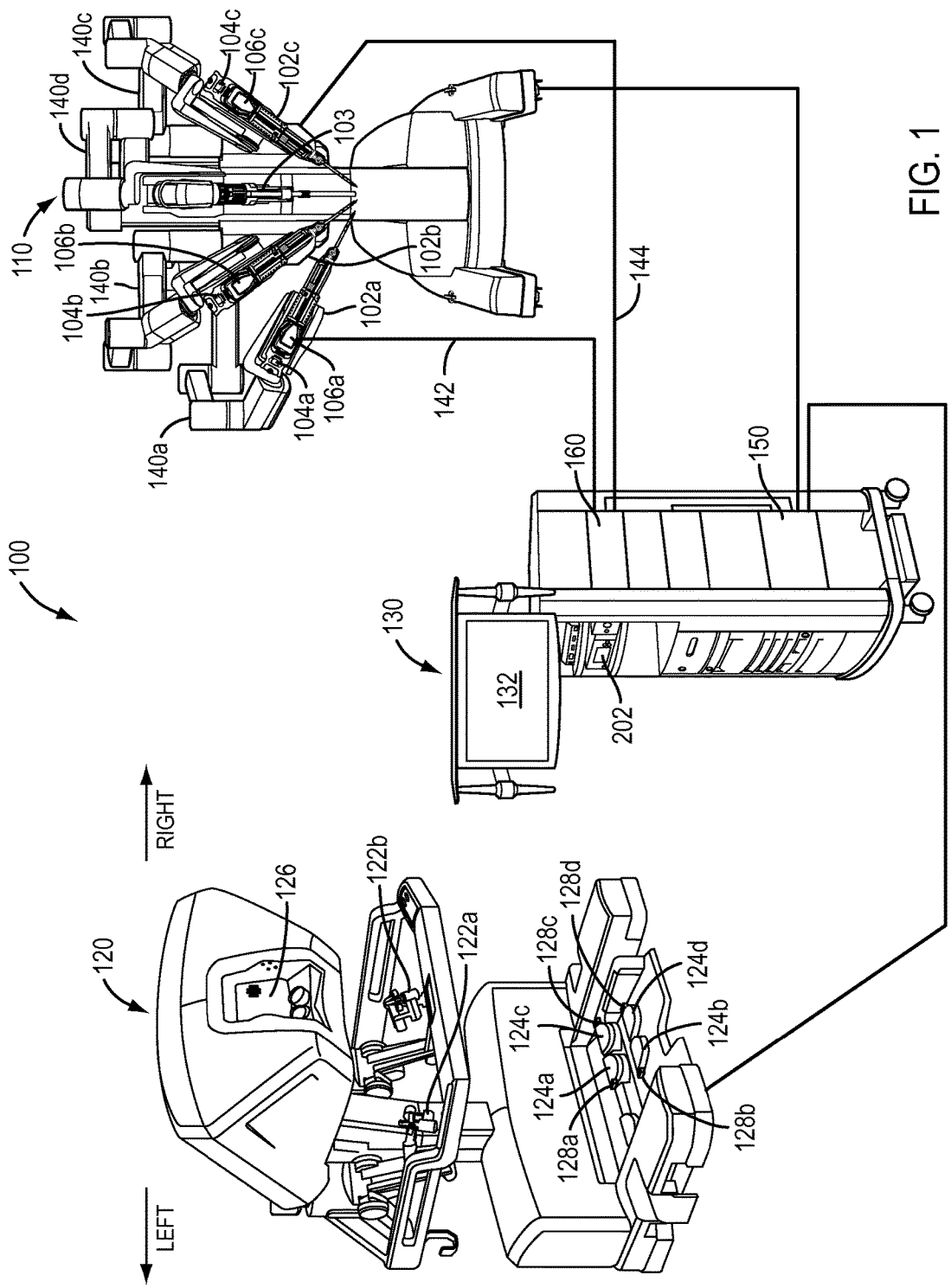
FIG. 1 is a diagrammatic view of an exemplary teleoperated surgical system in accordance with at least one exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures, and techniques have not been shown or described in detail so as not to obscure the disclosure. Like numbers in two or more figures represent the same or similar elements.

Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations.

With regard to the relative "left" and "right" positions of components of the surgical system, in general the reference frame is taken to be relative to a user in an operating position at the surgeon console; by way of example, reference is made to the exemplary embodiment of FIG. 1 that depicts relative right and left directions that occur based on a reference frame of a user in an operating position at the surgeon console.

In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Some existing robotic surgical systems use a functional mapping scheme in which each of the auxiliary input devices that operate auxiliary functions, such as energy supply, clamping, stapling, cutting etc., is assigned to a particular auxiliary function or functions that the auxiliary input device can activate at a surgical instrument. By way of example, one or more separate auxiliary input devices may control monopolar energy supplies (e.g., for cutting and/or coagulation), bipolar energy supply (e.g., for vessel sealing), suction, irrigation, laser energy supply, etc. performed by the surgical instrument. Thus, when a particular auxiliary function is desired to be performed by a surgical instrument, the surgeon activates the auxiliary function input device or set of auxiliary function input devices dedicated to the specific auxiliary function or changes the function to another of the auxiliary functions dedicated to the auxiliary function input device(s).

As used herein the terms "auxiliary function", "auxiliary input device" and variations thereof is intended to mean functions of the surgical instrument that are controlled by input devices, e.g., that may be remotely located such as at a surgeon console, and in some cases by redundant controls located at an instrument itself, but that are not functions that are controlled by input devices based on a master-slave control functionality over the surgical instruments such that the motion of the input device directly corresponds to the control of the movement or other functionality of the surgical instrument. The gripping input mechanisms are an example of the latter, master-slave type of control input device, while a foot pedal that is depressed to send a command signal to cause a surgical instrument at the patient side cart to delivery energy, activate a translating cutting blade, and/or fire a stapler, for example, is an example of the latter, auxiliary function input device. Auxiliary input devices can be chosen from a variety of input device structures, including foot pedals, buttons, triggers, joysticks, keyboards, and other input device mechanisms those having ordinary skill in the art are familiar with. Moreover, while various exemplary embodiments herein describe the use of foot pedals located at a surgeon console, auxiliary input devices are not so limited and the disclosure contemplates placement of auxiliary input devices of various structures at other locations, including being located as part of the master input devices. Examples of the latter could include, but are not limited to, triggers and/or slide switches place on master input devices (e.g., gripping mechanisms).

It may be desirable for various reasons to perform medical procedures by controlling one or more surgical instruments simultaneously. However, the number of auxiliary function input devices may be limited by the space considerations, such as at the surgeon console in a teleoperated surgical system or in proximity to the patient in a manual surgical system. Thus, it may be desirable to have a limited number of auxiliary function input devices (e.g., foot pedals) that are able to implement more auxiliary functions of surgical instruments than there are auxiliary function input devices.

In some cases, if multiple auxiliary functions are pre-assigned to particular auxiliary function input devices, conflicts arise if more than one surgical instrument to be used together are each assigned to the same auxiliary function input device or set of auxiliary function input devices. By way of example, a harmonic shears function for a harmonic shears surgical instrument may be assigned to a pedal positioned in a right bank of pedals at the surgeon console, and a monopolar electrocautery function for a monopolar electrosurgical instrument may also be assigned to the same pedal positioned at the right bank of pedals. Thus, the two instruments in this scheme—the harmonic shears and the monopolar electrosurgical instrument—are not able to be simultaneously controlled as each is assigned to the same auxiliary function input device (e.g., pedal).

Various exemplary embodiments of the present disclosure provide a robust way to assign control over auxiliary functions to input devices without conflicts arising when more than one surgical instrument, including that implement the same auxiliary functions, are being used simultaneously. Further, the assignment may occur in a faster, more automated and less cumbersome manner than by requiring a user, during a surgical procedure, to have to assign auxiliary functions to the auxiliary function input devices that implement them. Moreover, various exemplary embodiments may achieve flexibility in configuring and operating the surgical system when auxiliary function input devices are not pre-assigned and static to control auxiliary function types, but instead are alterable during a surgical procedure "on the fly" to match the surgical instrument a user is controlling with a particular hand.

According to various exemplary embodiments, an auxiliary function input device configured to cause a surgical instrument to perform an auxiliary surgical function is assigned based on a position of the auxiliary function input device and which of a user's hand (i.e., a left hand or a right hand) manipulates a master input device to control the surgical instrument. More specifically, an auxiliary input device that is located at a relative left position, as compared to an auxiliary input device that is located at a relative right position, will be assigned to control the auxiliary function of a surgical instrument that is under master-slave control of a master input device that is manipulated by a user's left hand. Similarly, an auxiliary input device located at the relative right position will be assigned to control the auxiliary function of the surgical instrument that is under master-slave control of a master input device that is manipulated by a user's right hand.

Those having ordinary skill in the art will appreciate that during use, master input devices could be in a relative left or a relative right position with respect to each other, such as, for example, by crossing two gripping mechanisms laterally over each other. However, regardless of the positioning of the master input devices with respect to each other, their manipulation by a surgeon's left or right hand to control the manipulation of a surgical instrument can be relied on as the basis for assigning which of a plurality of auxiliary input devices is to be automatically and operably coupled to control the auxiliary function of a surgical instrument. Using this positional-based assignment of the auxiliary input devices, when two surgical instruments are used together, one or more auxiliary functions for each of the surgical instruments is assigned to a separate auxiliary function input device based on the relative positions of the auxiliary function input devices and the user's hands providing master input to control the surgical instruments so that the auxiliary functions for different surgical instruments are not assigned to the same auxiliary function input device. In this manner, conflicts that arise from functionally mapping the input devices and the auxiliary functions of surgical instruments may be avoided, and a dynamically configurable system may be achieved.

As various exemplary embodiments described herein dynamically and automatically assign auxiliary control functions to auxiliary input devices based on the type of surgical instrument(s) currently being controlled as a slave instrument to a master input device (sometimes referred to as "in-following"), instead of assigning preset, static auxiliary functions to the auxiliary input devices. This dynamic assignment can provide a more intuitive relationship may occur between the control of the movement of the surgical instrument by relying on the user's hand operating a particular master input device and the activation of an auxiliary input device (e.g., foot pedal) having the same relative right or left positioning as the user's hand operating a respective instrument. Further, the positional mapping of auxiliary input devices to control auxiliary functions of surgical instruments contemplated by various exemplary embodiments is readily accomplished when a surgeon has a first instrument in-following with one of the surgeon's hand, e.g., the left hand, and drops that first instrument to pick up control over a second instrument previously not in an in-following state with that same hand. Even if the first and second instrument are of two differing auxiliary function types, the system automatically and dynamically can assign an auxiliary input device to control the auxiliary function of the newly in-following instrument based on the positional mapping described herein. As above, this may facilitate the user experience and add flexibility to the overall operation of the system.

Thus, for example, various exemplary embodiments of the present disclosure contemplate that when a user is manipulating a surgical instrument using a master input device, e.g., a gripping input device, operated by the user's left hand, auxiliary functions for that surgical instrument are implemented by one or more auxiliary function input devices, e.g., foot pedals, positioned relatively toward a left-hand side of a group of auxiliary function input devices (e.g., at a left bank of the group of input devices). If a user also is manipulating another surgical instrument using a master input device, e.g., a gripping device, operated by the user's right hand, auxiliary functions for that surgical instrument are implemented by one or more auxiliary function input devices, e.g., foot pedals, positioned relatively toward a right-hand side of a group of auxiliary function input devices (e.g., at a right bank of the group of auxiliary function input devices).

The positional mapping according to various exemplary embodiments of the present disclosure also permits a user that is controlling a first instrument in the right hand via a first master input device and a second instrument in the left hand by a second master input device to swap the control over the instruments (i.e., the first instrument to the left hand and second master input device and the second instrument to the right hand via the first master input device) during a procedure, while automatically also swapping the original assignment of the auxiliary input devices associated with the auxiliary functions of the instruments. That is, since the positional mapping of auxiliary input devices to control over surgical instruments is based on detecting which of a user's hands is currently controlling a surgical instrument, when the surgical instruments are switched to being controlled by different hands of the user during the procedure, the same intuitive mapping of the auxiliary input devices (based on position as further explained herein) can be retained without the user having to think through which auxiliary input device is preassigned to an instrument. Thus, the auxiliary input device positioned to the right of another auxiliary input device will always be assigned to control whatever instrument the user's right hand is operating at the time, and vice versa.

Further, various exemplary embodiments of the present disclosure contemplate detecting the type of the auxiliary function of a surgical instrument or instruments that are currently in-following and assigning to the respective auxiliary input devices that are positionally mapped to those surgical instruments an auxiliary function based on the detected instrument auxiliary function type. Thus, in accordance with various embodiments, in an automated and robust manner auxiliary functions can be assigned to auxiliary function input devices. Additionally, various exemplary embodiments contemplate that, because the auxiliary function(s) for each of the surgical instruments being controlled are assigned to a designated set of auxiliary function input devices, more than one instrument of the same auxiliary function type, such as, for example, more than one bipolar electrosurgical instrument, may be able to be in-following together and separately activated to perform their auxiliary functions.

Various exemplary embodiments also contemplate simplifying the user experience by eliminating the need for users to reassign auxiliary functions to different auxiliary input devices when auxiliary functions for more than one instrument that are to be simultaneously controlled are each assigned to the same auxiliary function input device. Instead, the system automatically makes the assignment based on the position of an auxiliary function input device and which of a user's left and right hand is operating a master input device with which the instrument to perform the auxiliary function is in-following.

Robotic Surgical System

With reference now to FIG. 1, a teleoperated surgical system 100 is provided which, in an exemplary embodiment, performs minimally invasive surgical procedures by interfacing with and controlling a variety of remotely operated surgical instruments 102a-102c. The surgical instruments 102a-102c may be selected from a variety of instruments that are configured to perform various surgical procedures, and in accordance with various exemplary embodiments one or more can be electrosurgical instruments, for example, bipolar and/or monopolar electrosurgical instruments. Some surgical instruments can also be so-called mixed mode, which permit the delivery of both monopolar and bipolar energy.

Monopolar electrosurgical instruments typically deliver electrical energy through a single pole and a return electrode that returns electrical energy back to an energy generator disposed externally to the patient. Examples of monopolar electrosurgical instruments include, but are not limited to, hooks, spatulas, shears including two blades energized with the same electric potential, cautery probes, irrigators, scissors, etc. Bipolar electrosurgical instruments typically deliver electrical energy through two poles separately, and the return path for the current is from one pole through the other pole. Examples of bipolar instruments include, but are not limited to, graspers, forceps, clamps, etc., which are generally used for sealing vessels and vascular tissue, grasping vessels, cauterizing or coagulating tissue, etc. Other types of energy (e.g., ultrasound, laser and/or nerve stimulation) also may be delivered to the patient through surgical instruments mounted at the patient side cart.

Of course the surgical instruments 102a-102c are not necessarily limited to instruments that deliver energy, but can be a variety of types of instruments that perform various auxiliary functions or not. Those having skill in the art will appreciate that although the description of exemplary embodiments below focuses on electrosurgical instruments, the present disclosure is not so limited and surgical instruments having a variety of auxiliary functionalities can be used in accordance with the principles set forth herein.

Nonlimiting examples of types of auxiliary functions encompassed by the present disclosure with appropriate modification to components include, for example, electrical energy delivery, e.g., cautery, laser, ultrasound, or radio frequency energy; fluid (e.g., liquids or gases) delivery (e.g., irrigation); image and/or audio streams; suction; cutting (e.g., harmonic shears or a cutting blade); clamping; stapling; cryogenic delivery features, etc.

As illustrated in the schematic view of FIG. 1, the robotic surgical system 100 includes a patient side cart 110, a surgeon console 120, and auxiliary/control cart 130. In non-limiting exemplary embodiments of the robotic surgical system 100, the auxiliary/control cart 130 includes "core" processing equipment, such as core processor 150, discussed below, and/or other auxiliary processing or function generating equipment, which may be incorporated into or physically supported at the control cart 130. The control cart 130 may also include other controls for operating the robotic surgical system. As will be discussed in more detail below, in an exemplary embodiment, signals transmitted from surgeon console 120 may be transmitted to one or more processors at control cart 130, which may interpret the signals and generate commands to be transmitted to the patient side cart 110 to cause manipulation of one or more of surgical instruments 102a-102c via manipulator interface assemblies 104a-104c to which the surgical instruments are coupled at the patient side cart 110. In addition to surgical instruments 102a-102c being mounted at the patient side cart 110, in various exemplary embodiments, an endoscopic imaging device 103 can be mounted to one of the patient side manipulator arms 140d to provide real-time images of a remote surgical site.

It is noted that the system components in FIG. 1 are not shown in any particular positioning and can be arranged as desired, with the patient side cart 110 being disposed relative to the patient so as to effect surgery on the patient. A non-limiting, exemplary embodiment of a teleoperated surgical system with which the instruments 102 can be utilized is a da Vinci® Si (model no. IS3000) commercialized by Intuitive Surgical, Inc. of Sunnyvale, Calif.

In operation, the surgeon console 120 receives inputs from a user, e.g., a surgeon, by various master input devices, including but not limited to, gripping mechanisms 122a, 122b and by various auxiliary input devices, including but not limited to foot pedals 124a-124d, etc. Through the master input devices, the surgeon console 120 serves as a master controller by which the instruments 102a-102c, 103 mounted at the patient side cart 110 act as slaves to implement the desired motions of the surgical instrument(s), and accordingly perform the desired surgical procedure. For example, while not being limited thereto, the gripping mechanisms 122a, 122b (also referred to as master tool manipulators) may act as "master" input devices that may control the surgical instruments 102a-102c, 103, for example, end effectors and/or wrists of the surgical instruments 102a-102c, 103, which may act as the corresponding "slave" devices mounted at the patient side manipulator arms 140a-140d. In the embodiment of FIG. 1, gripping mechanism 122a is situated on the left side of the surgeon console 120 and is generally arranged and positioned to be manipulated by a user's left hand to result in corresponding movement of an instrument at the patient side cart 110, as will be discussed in more detail below. Gripping mechanism 122b is situated on the right side of the surgeon console 120 and is generally arranged and positioned to be manipulated by a user's right hand to result in corresponding movement of an instrument at the patient side cart 110.

Further, while not being limited thereto, the foot pedals 124a-124d may be actuated to activate any of a variety of auxiliary functions of the surgical instruments 102, 103 that may be mounted at the patient side cart 110. Nonlimiting examples of such auxiliary functions include, for example, monopolar or bipolar electrosurgical energy, laser energy, ultrasound energy, radio frequency energy, nerve stimulation energy, image and/or audio streams, suction, fluid irrigation (e.g., through supply of gas or fluid), stapling, clamping, cutting, cryogenic application, etc. The foot pedals 124a-124d may be arranged in sets, e.g., "banks", of pedals such that, as will be described in more detail below, one set of pedals may be assigned to activate auxiliary functions for one of the surgical instruments 102a-102c, 103. While not being limited thereto, according to various exemplary embodiments, foot pedals 124a and 124b may be considered to be a "left bank" of pedals, while foot pedals 124c and 124d may be considered to be a "right bank" of pedals. In general any number pedals may be positioned in a right bank or left bank at the surgeon console 120. Those having ordinary skill in the art will appreciate, based on the arrangement and location of pedals 124a-124d shown in FIG. 1, that pedals can have a relative left positioning (e.g., pedals 124a, 124b) while being positioned more toward an overall right-hand side of the surgeon console 120. In this way, a relative left or right positioning is with reference to other banks of pedals (or other similar auxiliary function input devices). Moreover, those having ordinary skill in the art would appreciate that a bank of pedals can include any number of pedals including one, but is intended to encompass pedals similarly relatively positioned toward a left side or a right side relative to other pedals.

In various exemplary embodiments, the surgeon console 120 also includes output units including, but not limited to, a viewer or display 126 that allows the surgeon to view an image (e.g., a 2-dimensional and/or a 3-dimensional image) of the surgical site, for example, during the surgical procedure, e.g., via the optical endoscope 103 at the patient side cart 110. Other output units may include a speaker (or other component capable of transmitting sound), and/or a component with which a surgeon is in contact that can vibrate or the like to provide haptic feedback. In various exemplary embodiments, the one or more output units may be part of the surgeon console 120 and signals can be transmitted from the control cart 130 thereto. Although in various exemplary embodiments, one or more master input devices 122a, 122b or auxiliary input devices 124a-124d may be integrated into the surgeon console 120, various other master and/or auxiliary input devices may be added separately and provided so as to be accessible to the surgeon during use of the system, but not necessarily integrated into the surgeon console 120. In the context of the present disclosure, input mechanisms so located are considered part of the surgeon console.

Thus, a "surgeon console" as used herein includes a console that comprises one or more input devices 122a, 122b and 124a-124d that a surgeon can manipulate to transmit signals, generally through a control processor, e.g., such as part of control cart 130 described in more detail below, to actuate a remotely-controllable kinematic structure (e.g., surgical instruments 102a-102c and endoscopic imaging device 103 mounted at manipulator arms 140a-140d) at the patient side cart 110. The surgeon console 120 may also include one or more output devices that can provide feedback to the surgeon. As used herein, it should be understood, however, that a surgeon console can include a unit (e.g., substantially as shown by element 120 in FIG. 1) that integrates the various input and output devices, with, for example, a display, but also can include separate input and/or output devices that are in signal communication with the controllers, such as controllers provided at the control cart and accessible by a surgeon, although not necessarily integrated within a unit with various other input devices. As an example, input units may be provided directly at the control cart 130 and may provide input signals to a processor at the control cart. As such, a "surgeon console" does not necessarily require all of the input and output devices to be integrated into a single unit and can include one or more separate input and/or output devices.

Further, it is contemplated as within the scope of the present disclosure that master input devices can have a variety of forms, with the gripping mechanisms 122a, 122b that are mounted to the surgeon console 120 being only exemplary and nonlimiting. For example, master input devices, rather than being coupled to a surgeon console via mountings that are positioned toward a relative left and relative right position of the surgeon console could be free-floating but have a specific configuration to be operated by a user's right hand or left hand. In another alternative, a sensor, such as an optical sensor for example, may be used to determine which of a user's hands (i.e., left or right) is operating a master input device, regardless of its specific configuration. Also, it is contemplated that various sensor technology that can sense and track the motion of a user's hands can be implemented for use as master input devices. Using such sensor technology may permit the detection of the motion of a user's left hand or right hand to determine which hand is controlling which instrument. An exemplary embodiment of sensor technology configured for sensing and tracking motions of a user's hand includes the sensor technology developed by Leap Motion, Inc. Accordingly, master input devices and the determination of which of a user's hands is operating a master input device is not limited to the gripping mechanism configuration of the system 100 shown in FIG. 1.

Figure 2:
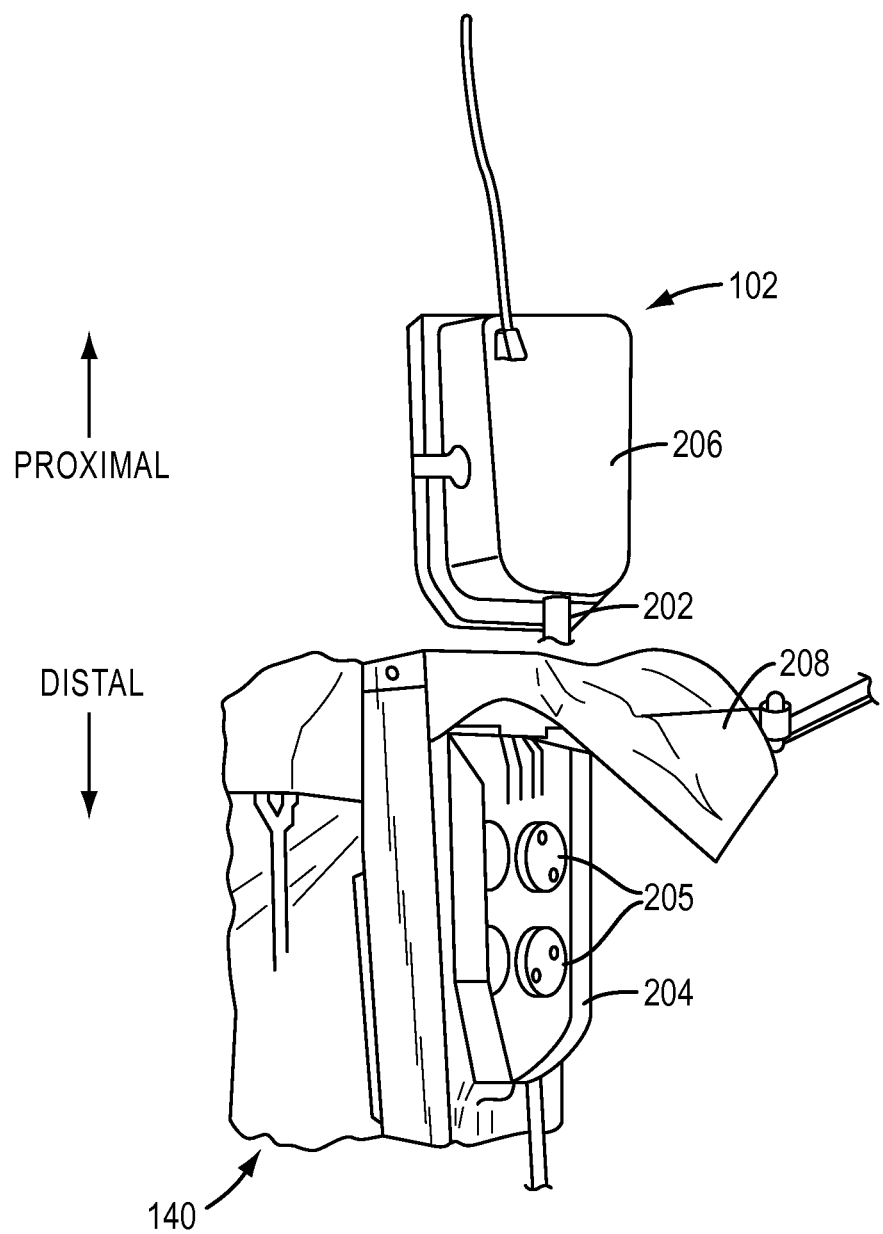
FIG. 2 is a perspective view of an actuation interface assembly at a patient side cart of a robotic surgical system in accordance with at least one exemplary embodiment.
Figure 3:
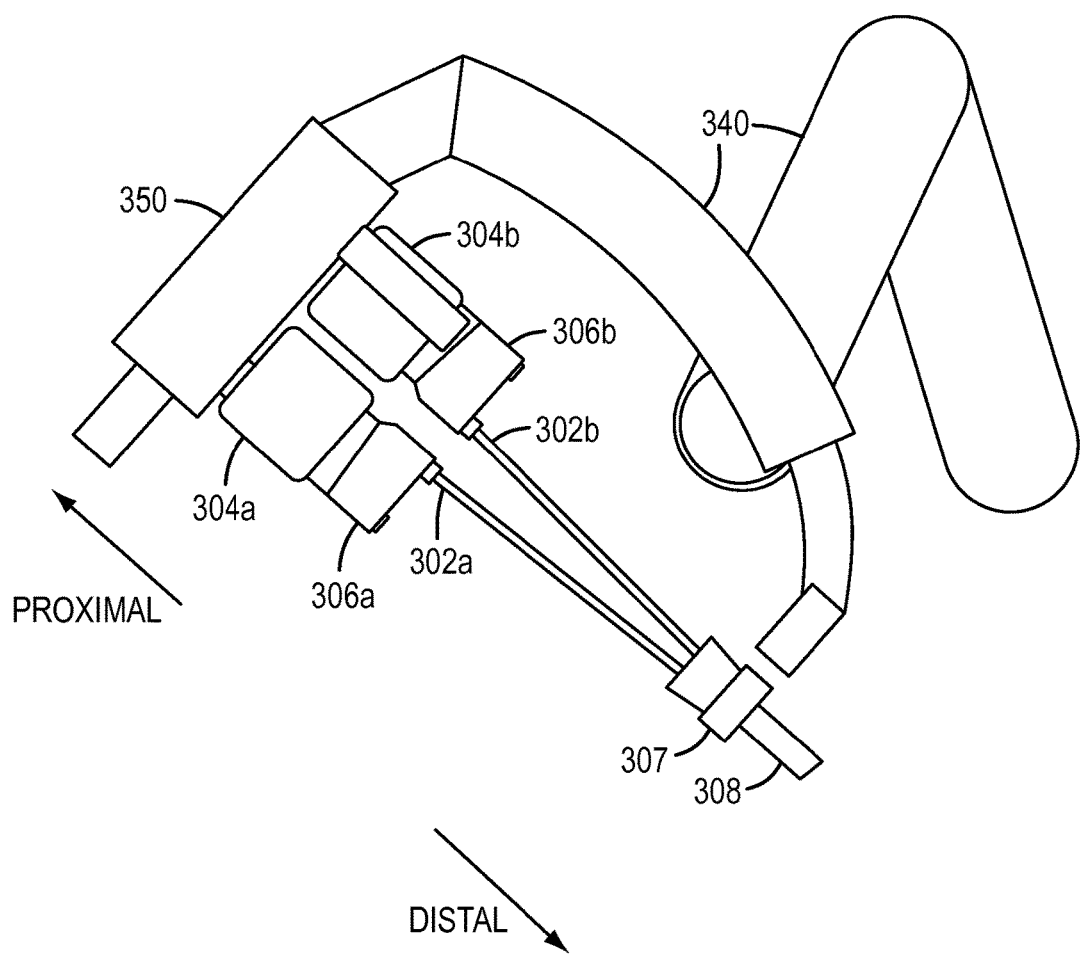
FIG. 3 is a partial schematic view of another exemplary embodiment of a manipulator arm of a patient side cart with two electrosurgical instruments in an installed position.

The exemplary embodiment of FIG. 1 illustrates a patient side cart 110 with multiple, independently moveable manipulator arms 140a-140d that may each support an manipulator interface assembly 104 (an exemplary such assembly 204 shown in part in FIG. 2) and are configured to hold and manipulate various the surgical instruments (e.g., surgical instruments 102a-102c) mounted thereto. However, those having ordinary skill in the art will appreciate that other patient side cart configurations aside from that depicted in FIG. 1 may be used, such as in the exemplary embodiment of FIG. 3. In FIG. 3, a patient side cart can have a single manipulator arm 340 (the arm portion being shown in isolation in FIG. 3) with a base 350 that can support plurality of surgical instruments 302a, 302b (only two being shown in FIG. 3 for simplicity) at plural manipulator interface assemblies 304a, 304b (again only two being shown for simplicity), which interface with transmission mechanisms housed in transmission housings 306a, 306b of multiple surgical instruments 302a, 302b. In the exemplary embodiment of FIG. 3, the distal portions of the mounted instruments 302a, 302b are received through an entry guide structure 307 that may lead to a cannula 308 that is introduced into the patient's body at a single incision site or "port." Although not depicted in FIG. 3, the distal end portions of the instruments can exit out of the distal end of the cannula 307 (or other access structure) to access the remote surgical site. It is noted that in the exemplary embodiment of FIG. 1, there may be plural separate incision sites or "ports" to introduce all of the mounted instruments (e.g., four to accommodate the surgical instruments 102a-102c and the endoscopic imaging device 103).

While four manipulator arms 140a-140d are shown in FIG. 1 and a single manipulator arm 340 is shown in FIG. 3, one of ordinary skill would recognize that the principles of the present teachings would apply irrespective of the number of patient side manipulator arms and the present disclosure may apply to more or less than four patient side manipulator arms or more than a single patient side manipulator arm with multiple manipulator interface assemblies.

Based on the commands input to master input devices, such as gripping mechanisms 122a, 122b at, for example, the surgeon console 120, the patient side cart 110 can position and actuate the instruments 102a-102c and 103 to perform a desired medical procedure. For example, as the gripping mechanisms 122a, 122b are manipulated, two of the manipulator arms 140a-140d that are actively and respectively associated with the gripping mechanisms 122a, 122b at the patient side cart 110 manipulate their respectively mounted surgical instruments 102a-102c. Further, the gripping mechanisms 122a, 122b can cause the actuation of the instruments 102a-102c, 103 such as a wrist or end effector thereof if any, via the manipulator interfaces assemblies, such as manipulator interface assembly 104, 204 shown in FIGS. 1 and 2, and manipulator interface assemblies 304a, 304b shown in FIG. 3, which are configured to engage with transmission housings 106a-106c, 206 (shown in isolation in FIG. 2), 306a-306b provided at a proximal end of each of the surgical instruments 102a-102c, 202, 302a-302b. Those having ordinary skill in the art are familiar with such transmission housings of robotic surgical instruments that house a variety of gearing and force transmission mechanisms that are actuated by actuators of the manipulator interface assembly, such as actuators 205 of the manipulator interface assembly 204 shown in FIG. 2. "Proximal" and "distal" directions are shown in FIGS. 2 and 3 relative to the surgical instrument.

The surgical instruments via their transmission housings can be mechanically and/or electrically coupled to the manipulator interface assemblies to be able to operate the instruments. According to at least one exemplary embodiment, as shown in FIG. 2, a sterile drape 208 may be provided between the patient side cart 110, particularly over the manipulator arms 140a-140d, and the surgical instrument 102 in order to create a sterile boundary between the sterile field. The manipulator interface assembly 204 also may have a sterile adapter face to engage with a sterile surgical instrument transmission housing 206 (labeled 106a-106d in FIG. 1). It is noted that the transmission housing 206 is shown in isolation, not engaged with the manipulator interface assembly 202, with the instrument shaft 202 shown in part in FIG. 2.

The control system receives and transmits various control signals to and from the patient side cart 110 and the surgeon console 120, and can transmit light and process images (e.g., from the endoscopic imaging device 103 at the patient side cart 110) for display, such as, e.g., display 126 at the surgeon console 120 and/or on a display 132 associated with the control cart 130.

The control cart 130 may include at least one processor, e.g., core processor (or controller) 150 that controls the operation of the surgical instruments 102a-102c and the endoscope 103 installed at the patient side cart 110 and the patient side manipulator arms 140a-140d to which the surgical instruments 102a-102c and endoscope 103 are coupled. In an exemplary embodiment, the core processor 150 can control the implementation of an auxiliary function of a surgical instrument 102, such as energy (e.g., laser, ultrasound, electrosurgical, nerve stimulation etc.) and/or other flux delivery (irrigation, suction) and/or clamping, cutting, stapling, and/or other auxiliary operation.

In exemplary embodiments, the control system may have all control functions integrated in one or more processors, such as core processor 150 at the control cart 130, or additional controllers may be provided as separate units and/or supported (e.g., in shelves) on the control cart 130 for convenience. The latter may be useful, for example, when retrofitting existing control carts to control surgical instruments requiring additional functionality, for example, by providing electrical energy for use in monopolar and bipolar applications. For example, the control cart 130 may include an electrosurgical unit (ESU) 160, which can provide flux sources, such as monopolar and bipolar energy sources, may be provided as separate unit(s) from the core processor 150 and supported on the control cart 130. In various exemplary embodiments, the ESU 160 may be disposed to transmit to and receive signals from the core processor 150. In an alternative embodiment, the core processor 150 and the components of the ESU 160, which can provide flux sources, such as monopolar and bipolar energy sources, can be incorporated together at the control cart 130 as a single integrated unit, within which at least one of the components of the ESU 160 may be in communication to receive signals to and from the core processor 150.

One of ordinary skill in the art would recognize that the controllers, e.g., core processor 150, provided at control cart 130 may be implemented as part of a control system, which, as will be discussed in more detail below, controls various functions of the present disclosure. One of ordinary skill in the art would recognize that functions and features of the controllers, e.g., core processor 150, may be distributed over several devices or software components, including, but not limited to, processors at any of the surgeon console 120, patient side cart 110 and/or other devices, such as ESUs, incorporating processors therein. Functions and features of the control system, which may include core processor 150, may be distributed across several processing devices.

Positional Mapping System and Method

In the description that follows, various exemplary embodiments describe the mapping of auxiliary input devices with surgical instruments such as surgical instruments 102a-102c of FIG. 1. Those having ordinary skill in the art would appreciate, however, that other types of instruments, such as an imaging instrument (e.g., endoscopic camera instrument 103 in FIG. 1) also can be controlled through auxiliary input devices and the positional mapping described herein; accordingly, as used in the claim, surgical instrument should not be limited to a particular form of instrument, but should be broadly construed to encompass various instruments of a surgical system used to perform a surgical, diagnostic, or therapeutic procedure and controlled remotely, as has been described above.

Figure 4:
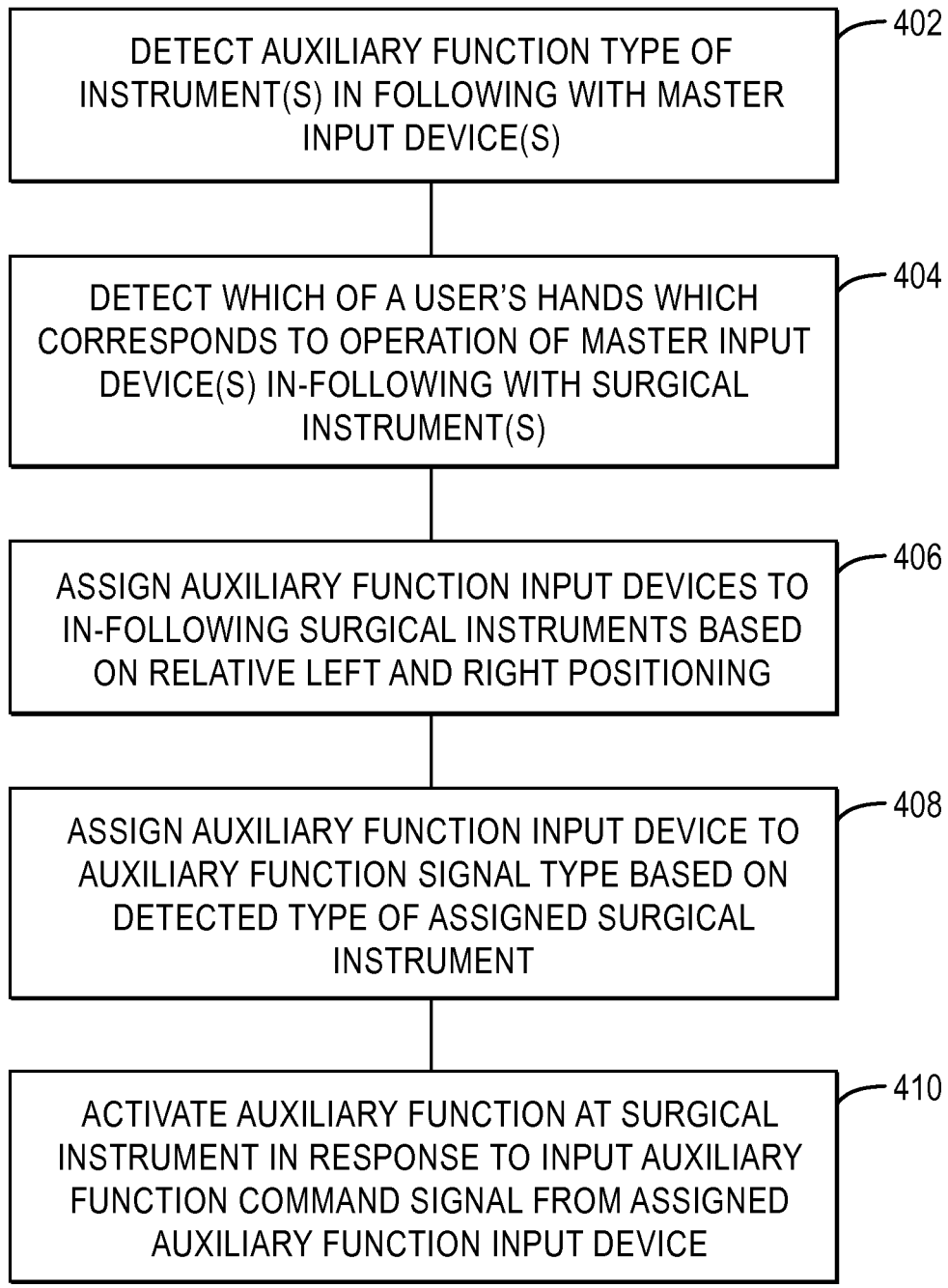
FIG. 4 is a flow diagram illustrating an exemplary workflow for assigning control of auxiliary surgical functions of surgical instruments to auxiliary function input devices of a teleoperated surgical system in accordance with at least one exemplary embodiment.

A flow diagram that depicts exemplary steps of a workflow in accordance with various exemplary embodiments is shown in FIG. 4. It should be understood that each of the steps depicted may not be required in any particular embodiment and some of the steps depicted may occur in other orders and/or more than once than those illustrated.

For ease of understanding, the exemplary workflow of FIG. 4 is described below with reference to implementation on various components of the exemplary embodiment of FIG. 1. However, those having ordinary skill in the art will appreciate that such description with reference to FIG. 1 is not intended to be limiting, and the workflow of FIG. 4 can be implemented on a variety of robotic surgical systems, including a surgical system having a patient side cart configuration like that of FIG. 3, for example.

With reference now to FIG. 4, in at least one exemplary embodiment, the teleoperated surgical system 100 as shown and described in FIG. 1 can be used in the implementation of the present disclosure, which contemplates providing a method and system for assigning auxiliary functions, e.g., flux delivery, clamping, stapling, cutting, etc., to auxiliary function input devices at a surgeon console of a teleoperated surgical system. FIG. 4 is an exemplary embodiment of a workflow for automatically assigning auxiliary function control over surgical instruments to auxiliary function input devices. In various exemplary embodiments in accordance with the present disclosure, in the exemplary workflow of FIG. 4, at operation 402, a type of surgical instrument 102 is detected which is responsive to and in a slave control relationship with one of a plurality of master input devices, e.g., gripping mechanisms 122a, 122b. The respective surgical instrument 102a-102c that is responsive to a master input device is a state referred to as an "in-following" state, which is a state of the surgical instrument 102a-102c being actively controlled by one of the master input devices 122a, 122b.

For example, in some exemplary embodiments of robotic surgical systems encompassed within the scope of the present disclosure, there are fewer master input devices (e.g., two gripping mechanisms 122a, 122b at the surgeon side console 120) that are operable at a given time than there are manipulator interface assemblies, e.g., 104 (FIG. 1) or 304 (FIG. 3) with installed surgical instruments (e.g., three or more at the patient side cart 110, 310). In other embodiments, there may be more master input devices that are operable at a given time than there are manipulator interface assemblies with installed surgical instruments. Such a situation can occur, for example, in a dual surgeon console teleoperated surgical system setup, with which those having ordinary skill in the art are familiar. In any case, the surgeon side console 120 is used to identify to the control system which of the plurality of manipulator interface assemblies will be mapped and under control of a given master input device. With reference to the embodiment of FIG. 1, for example, the surgeon side console 120 identifies to the control system which of the manipulator interface assemblies 104a-104c is mapped in a current master-slave relationship with one of the two gripping mechanisms 122a, 122b and thus which mounted surgical instrument 102a-102c is in-following with each gripping mechanism 122a, 122b.

In an exemplary embodiment, manipulator interface assembly 104b at the manipulator arm 140b may be mapped to the left gripping mechanism 122a at the surgeon side console 120. When a manipulator interface assembly is in a master-slave relationship with a master input device, the manipulator interface assembly, and consequently the surgical instrument (e.g., 102b in this example) installed at that manipulator interface assembly, are designated as "in following" and a signal indicative of that status is provided to the control system, such as to processor 150 at control cart 130.

In some systems, an additional manipulator arm of the patient side cart 110, e.g., arm 140*a*, can swing around to be either positioned on a left side (as shown in FIG. 1) or a right side (not shown) of the patient side cart 110, and accordingly controlled by either the left master input device 122*a* or right master input device 122*b* depending on that position. For the description that follows, the manipulator arm 140*a* is shown and described in the left operational position shown in FIG. 1. In the exemplary embodiment of FIG. 3, the gripping mechanisms 122*a* and 122*b* may be placed in an in-following control relationship respectively with the manipulator interface assemblies 304*a*, 304*b* and consequently instruments 302*a*, 302*b* mounted thereto; although it should be noted that more than two manipulator interfaces may be provided in the embodiment of FIG. 3 and accordingly selectively placed in following with the master input devices.

According to various exemplary embodiments, the surgical instruments 102 include a unique identifier encoded at the surgical instruments that identifies the specific surgical instrument and the type of surgical instrument, including, for example, the auxiliary function(s) a surgical instrument can perform. The unique identifier may be, for example, a unique serial number for the specific surgical instrument 102. The unique identifier may be provided at one or more memory storage structures provided on the surgical instrument 102 and containing various information about the surgical instrument 102, such as for example, instrument type, number of uses, etc., as those skilled in the art are familiar with. By way of example, the memory storage structure at which the unique identifier is provided may be a transmitter, which may be wireless, e.g., a radio frequency identification (RFID) tag, at which is encoded the unique identifier.

The unique identifier may be transmitted from the surgical instrument 102 and sensed by one or more memory structure reader devices (not shown) at the patient side cart 110, for example, in proximity to or associated with each actuation interface assembly. According to exemplary embodiments, the memory structure reader device(s) may be provided at one or more support structures to which an actuation interface assembly is attached. Exemplary instrument reader devices can include, but are not limited to, for example, RFID sensors that read a unique RFID tag that is disposed on each surgical instrument; a memory chip (e.g., a SRAM or EEPROM memory chip) reader that can interface with and receive data from a unique memory chip provided on each surgical instrument; a barcode reader; and/or a magnetic medium reader (e.g., magnetic strip reader). Those having ordinary skill in the art will appreciate other types of reader devices can be used that have the ability to read stored information from a readable or readable and writable memory storage structure associated with the instrument. Such memory storage structure reader devices can be proximity-based in that their ability to read the unique information with which an instrument memory storage device is programmed relies on the instrument being in close range, e.g., coupled or engaged, with a respective actuation interface assembly of the patient side cart.

According to exemplary embodiments of the present disclosure, each of the manipulator arms 140*a*-140*d* having a manipulator interface assembly 104*a*-104*d* may include the receiver to sense the information transmitted by the transmitter at the surgical instrument 102. According to other exemplary embodiments, any of a variety of support structures that support a manipulator interface assembly can include an instrument reader device to sense the information transmitted by the transmitter at the surgical instrument 102. The transmitter and the receiver may both support various wireless communication protocols, with which those of ordinary skill in the art are familiar.

According to exemplary embodiments of the present disclosure, after the instrument reader device senses the unique identifier, the unique identifier information may be transmitted to the control system, which may include one or more processors 150 able to analyze the detected type of surgical instrument 102.

The unique identifier can be used to determine the instrument type and other information regarding an instrument 102 installed at the patient side cart 110. With regard to instrument type, according to exemplary embodiments, the unique identifier information associated with a respective surgical instrument can include whether or not it is a surgical instrument configured for flux delivery, such as energy delivery (e.g., an electrosurgical instrument), and what type of energy it is configured to deliver (e.g., bipolar, monopolar, mixed mode, etc.).

One of ordinary skill in the art would recognize that when data, such as the instrument identifier information, is received by a control system, the data may be received at one or more of the controllers or processors described above as part of the control system. Further, the receipt of and/or processing of the data may be distributed across one or more of the controllers or processors of the control system.

Instrument identification storage and reader device technology can be via a variety of technologies known to those skilled in the art, such as, for example, any of a variety of optical encoding/reading, radio-frequency encoding/reading, magnetic encoding/reading, digital (e.g., EEPROM and other similar storage devices/readers) encoding/reading, etc.

When the instrument identification information is provided to the core processor 150, the core processor 150 recognizes that the instrument identification information is associated with a specific manipulator interface assembly 104*a*-104*c* to which a particular instrument 102*a*-102*c* is mounted. This can be, for example, by virtue of the identifier reader being located in close proximity to the manipulator interface assemblies so as to be able to read identification tags only from an instrument mounted at the actuation interface assembly. Any structure to which the actuation interface assembly 104 is coupled, e.g., the manipulator arms 140, a support on the arms 140, an adapter of FIG. 2, etc. may be provided with the instrument identification reader to recognize the instrument identification signal. The control system is therefore able to determine that the instrument identification signal is associated with a specific manipulator interface assembly that is associated with the reader that read and transmitted the instrument identification signal.

According to various exemplary embodiments, the control system is configured to determine which of the manipulator interface assemblies 104 is in a master-slave relationship with which of the master input devices, e.g., gripping mechanisms 122*a*, 122*b*, and is also configured to detect that a specific surgical instrument 102 is installed at a particular manipulator interface assembly 104. Consequently, according to various exemplary embodiments, the teleoperated surgical system 100 is configured to determine which of the installed instruments 102*a*-102*c* is being controlled by which of the master input devices, e.g., gripping mechanisms 122*a*, 122*b*.

In various exemplary embodiments in accordance with the present disclosure, in the exemplary workflow of FIG. 4, at operation 404, the control system detects which of a user's hands is operating a master input device with which a surgical instrument 102 is in-following. For example, the control system may determine that instrument 102a is in-following with gripping mechanism 122a, which is operable by a user's left hand, and that instrument 102c is in-following with gripping mechanism 122b, which is operable by a user's right hand. As explained above, the determination of which of a user's hands operates a master input device can be detected in numerous ways, such as, the relative positioning and/or configuration of the master input devices, and/or via other sensing and tracking technology.

According to various exemplary embodiments, at operation 406 in the workflow of FIG. 4, the teleoperated surgical system 100 is configured to assign one or more auxiliary function input devices to operably couple (e.g., via signal communication) to and activate the in-following surgical instruments 102 based on a relative left or right positioning of the auxiliary function input device, as compared to another auxiliary function input device, and the respective user's hand operating the master input device controlling the in-following surgical instrument. The one or more auxiliary function input devices to which the auxiliary function(s) are assigned can, for example, be positioned in a left bank of pedals (e.g., 124a, 124b in FIG. 1) or a right bank of pedals (e.g., 124c, 124d) and thus positionally correspond respectively to a user's left hand or a user's right hand.

Further, in various exemplary embodiments, as depicted at 408, the control system may cause a particular auxiliary function signal type to be sent to the corresponding positionally mapped surgical instrument upon actuation of the assigned auxiliary function input device based on the auxiliary function type of the instrument detected at step 402.

By way of example, the teleoperated surgical system 100 may assign an auxiliary function, e.g., bipolar energy supply, in response to actuation of foot pedal 124a, which is in a left bank of foot pedals, when surgical instrument 102a is detected to be a bipolar electrosurgical instrument at step 402 and also is determined to be in-following with a left gripping mechanism 122a at step 404. As discussed above, a left bank of foot pedals may be considered, in the exemplary embodiment of FIG. 1, to include foot pedals 124a and 124b, and the right bank of foot pedals may be considered, in the exemplary embodiment of FIG. 1, to include foot pedals 124c and 124d. By way of further example, the foot pedal 124a which is assigned a control function based on the detected type of surgical instrument 102a has a relative position, e.g., to the left, with respect to other foot pedals 124c-124d that activate the surgical instruments to implement an auxiliary function. The relative position of the foot pedal 124a corresponds to a user's left hand that operates the master gripping mechanism 122a to output a signal to manipulate the surgical instrument 102a. Thus, the auxiliary function(s) for the surgical instrument 102a, which is controlled by the left-handed gripping mechanism 122a, are assigned to the left bank of the foot pedals that includes 124a, 124b in the exemplary embodiment of FIG. 1. By way of example, if the detected type of surgical instrument is a permanent cautery spatula, foot pedal 124a could automatically be assigned to send a signal to a monopolar energy generator to perform a monopolar cut auxiliary function and foot pedal 124b could be assigned to send a signal to a monopolar energy generator to perform a monopolar coagulation auxiliary function.

In various exemplary embodiments, assignments of auxiliary input devices to auxiliary function signal type can, in addition to positional and/or detected instrument type mapping, can also rely on accepted industry standards. By way of nonlimiting example, the auxiliary input devices can be colored and functional assignment can be based on those colors. For example, the foot pedals 124a-124d, may be either blue or yellow, with a blue pedal being be assigned to an energy delivery that results in a coagulation process and a yellow pedal being assigned to an energy delivery that results in a cutting process, when these are the functions that are available for an instrument(s) under control of the auxiliary input devices.

In various exemplary embodiments, at operation 410 of the work flow of FIG. 4, upon actuation of one of the auxiliary function input devices, e.g., foot pedals 124a-124d, an input command signal is output from the actuated auxiliary input device to core processor 150, for example, of the control system. Thereafter, the core processor 150 sends an auxiliary function activation signal to control the assigned and in-following surgical instrument 102 according to the surgical auxiliary function currently assigned to the actuated auxiliary function input device. By way of particular example, when foot pedal 124a is assigned to a surgical instrument 102a of a particular auxiliary function type and that is in-following with left gripping mechanism 122a, actuation (e.g., depressing) of the foot pedal 124a will cause the surgical instrument 102a to be activated to deliver monopolar cautery energy. If, however, rather than being a monopolar cautery energy delivery instrument, surgical instrument 102a instead is configured for stapling for example, then actuation of foot pedal 124a would activate the surgical instrument 102a to perform a stapling auxiliary function.

In various exemplary embodiments, with reference to FIG. 1, for example, the upper pedals 124a, 124c can activate a higher or stronger auxiliary function level than the lower pedals 124b, 124d. For example, if the surgical instrument type positionally mapped to the left bank of pedals 124a, 124b is a electrosurgical energy type of instrument, then depressing pedal 124a may activate the surgical instrument to deliver a higher voltage energy than depressing 124b would or vice versa. In other exemplary embodiments, upper and lower pedal pairs in a bank can correspond to differing modalities, such as, for example, monopolar cut and monopolar coagulation; stapler fire and stapler clamping; suction and irrigation; mechanical cutting, and vessel sealing, etc.

As further described below, the control system also can provide information to the user at the surgeon console, for example, at display 132, to inform the user what type of instrument is in-following with a particular master input device and also what auxiliary functions each of the auxiliary input devices is assigned to activate. With this information, the surgical system can be controlled intelligently by a user to carry out various surgical procedures.

Figure 5:
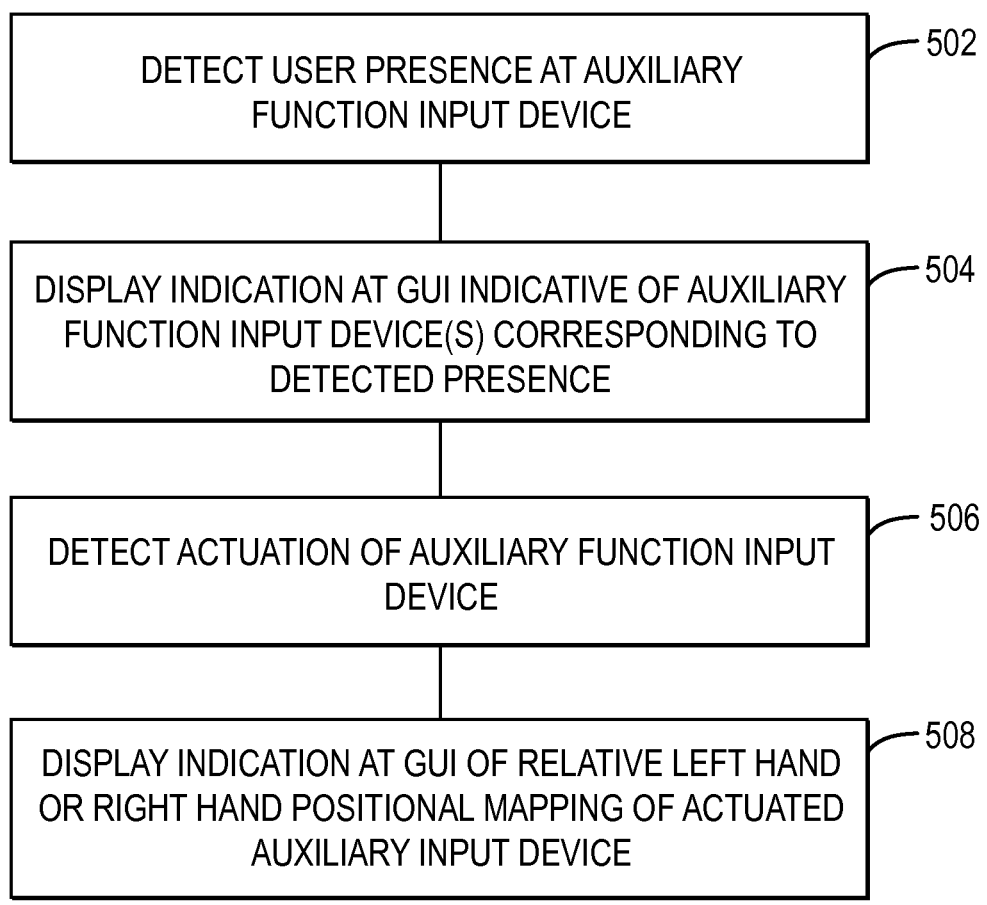
FIG. 5 is a flow diagram illustrating an exemplary workflow for displaying indications related to auxiliary function input devices on a graphical user interface in accordance with at least one exemplary embodiment.

A flow diagram that depicts exemplary steps of a workflow in accordance with various exemplary embodiments is shown in FIG. 5. It should be understood that each of the steps depicted may not be required in any particular embodiment and some of the steps depicted may occur in other orders and/or more than once than those illustrated. In one exemplary embodiment, for example, steps 506 and 508 can occur without 502 and 504 occurring.

Figure 6:
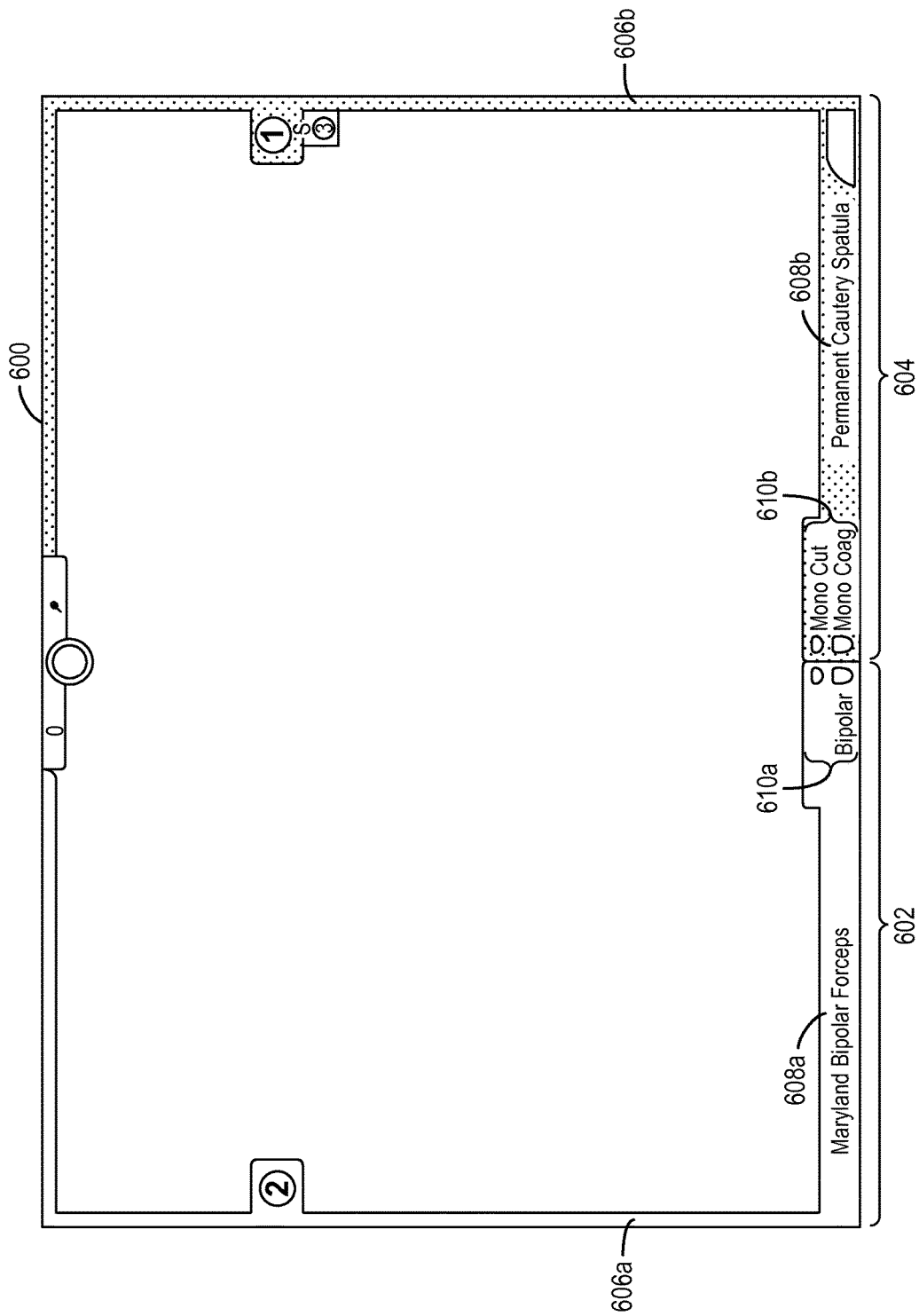
FIG. 6 is an exemplary screen of a graphical user interface in accordance with the present disclosure.
Figure 7:
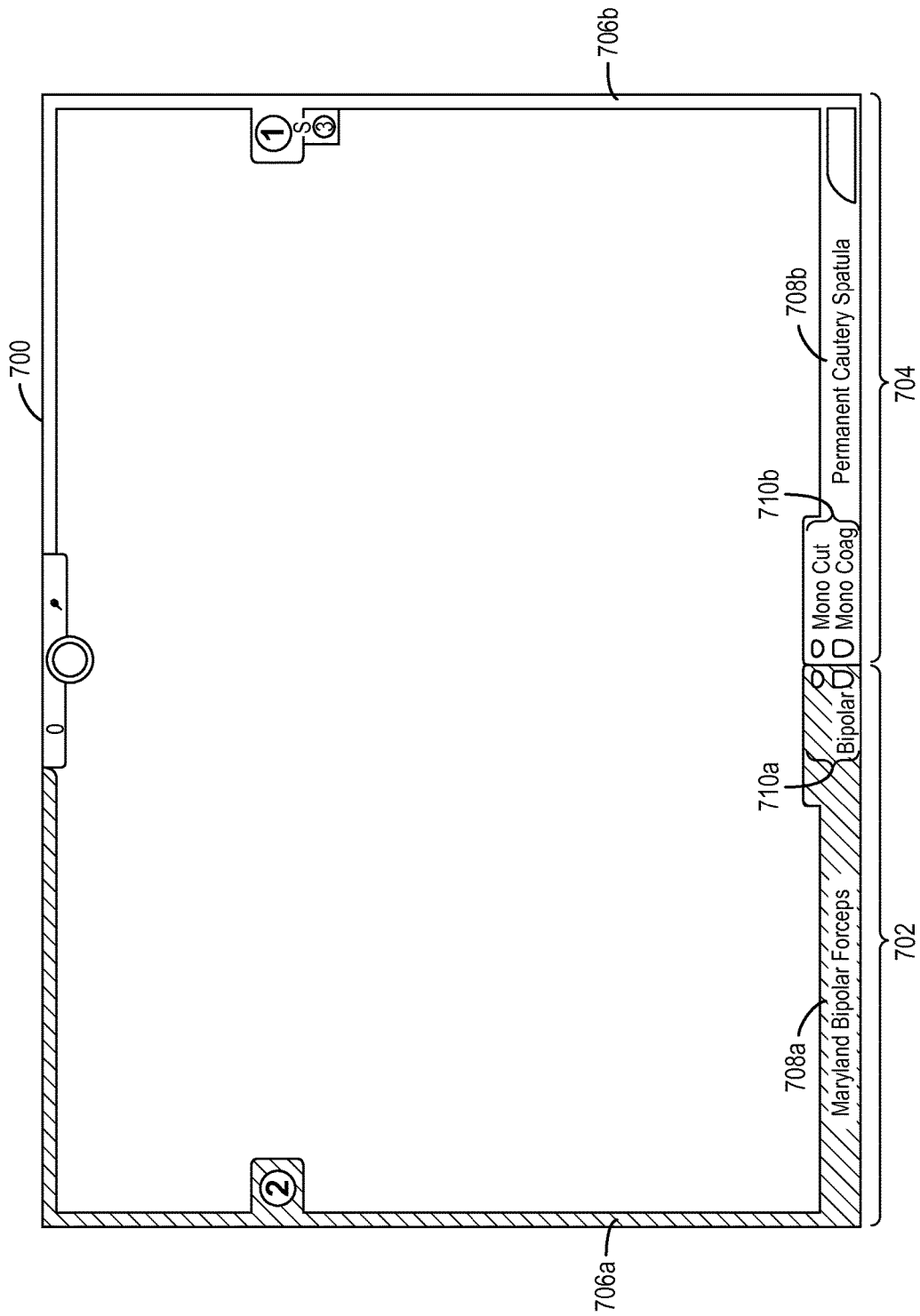
FIG. 7 is another exemplary screen of a graphical user interface in accordance with the present disclosure.

FIG. 5 is an exemplary embodiment of a workflow for displaying indications related to auxiliary function input devices on a graphical user interface, exemplary embodiments of which are shown in FIGS. 6 and 7. In various exemplary embodiments, the graphical user interface may be displayed on a display for visualization by a user of the teleoperated surgical system, such as a user at surgeon console 120. In accordance with the present disclosure, in the exemplary workflow of FIG. 5, at operation 502, a presence of a user is detected in proximity to one or more of the auxiliary function input devices, such as foot pedals 124a-124d. According to various exemplary embodiments, the presence of the user can be detected by the use of one or more presence sensors, for example, foot presence sensors 128a-128d, shown in FIG. 1, which may be provided at each of the foot pedals 124a-124d or may be provided in the relative vicinity of the foot pedals 124a-124d. In various exemplary embodiments, each pedal may have its own presence senor or groups of pedals (e.g., the left bank and the right bank respectively) could be associated with a shared presence sensor and thus only two of the sensors 128 depicted in FIG. 1 could be utilized. Regardless, the user is detected in the proximity of one or more foot pedals 124a-124d when, for example, the user's foot is detected over one or more foot pedals 124a-124d. By way of example, the user's foot may be detected hovering over the left bank of foot pedals 124a, 124b or over the right bank of foot pedals 124c, 124d.

Those having ordinary skill in the art would have familiarity with various types of sensing technology that may be implemented as the presence sensors with one nonlimiting example including a light emitter and optical detector arranged so that when a user's foot interrupts the light beam, the sensor sends a signal to the processor indicating that there is an object over the pedal(s) being sensed.

When the presence of a user, e.g., the user's foot (which can be either a right foot or a left foot), is detected over one or more of the foot pedals 124a-124d, the one or more foot presence sensors (e.g., one or more of sensors 128a-128d) that detects the user's presence transmits a presence detection signal indicating the user's presence. The presence detection signal may be received at one or more processors located at, for example, the surgeon console 120, or may be transmitted to, for example, the core processor 150 at the control cart 130. The processors receive the presence detection signal and output a signal to provide a display to a user, such as at display 132.

Turning now to FIGS. 6 and 7, exemplary portions of screen captures of a graphical user interface illustrating exemplary aspects of the present disclosure are depicted. FIGS. 6 and 7 each illustrates a graphical user interface (GUI) 600, 700, which can be provided at a display accessible by a user of the teleoperated surgical system 100. In an exemplary embodiment, the GUI 600, 700 may be provided at the display 126. However, one of ordinary skill in the art would recognize that the present disclosure is not limited thereto and the GUI 600, 700 may be provided at any display, such as display 132, for example, provided at the control cart 130 robotic surgical system 100. Also, the GUI 600, 700 may be displayed at more than one of display associated with the system.

Moreover, for simplicity only portions of the GUI displays 600, 700 that make up the overall display are shown. In general, the main part of the display, shown blank in FIGS. 6 and 7, may be displaying images from the endoscopic camera, which can include images of the surgical site and/or the relevant in-following surgical instruments, for example.

The GUI 600, 700 including a left side 602, 702 and a right side 604, 704 of the GUI 600, 700 may, in accordance with exemplary embodiments, provide indication bars 606a, 706a and 606b, 706b which may each be highlightable (illustrated by the shading in FIGS. 6 and 7), as will be described in more detail below. The indication bar 606a, 706a may be provided at a portion or along the entirety of an outer portion of the left side 602, 702 of the GUI 600, 700 and the indication bar 606b, 706b may be provided at a portion or along the entirety of an outer portion of the right side 604, 704 of the GUI 600, 700. One of ordinary skill in the art would recognize that the present disclosure is not limited to, for example, indication bars and is not limited to being provided at an outer portion of the GUI 600, 700 and any of a variety of indicators may be provided at the GUI 600, 700 that provide a user with the ability to distinguish between the relatively positioned sides (i.e., left and right) of the GUI 600, 700. For example, an indicator may highlight the entire left side 602, 702 or right side 604, 704, or a portion thereof, of the GUI 600, 700.

The GUI 600, 700 may also include a left instrument identification display 608a, 708a and a right instrument identification display 608b, 708b, which indicate to the user the type of instrument currently responsive to the master input devices, e.g., in-following with gripping mechanism 122a, 122b. In the examples shown in FIGS. 6 and 7, the left instrument identification display 608a, 708a shows that the instrument controlled by the left gripping mechanism 122a (and thus the user's left hand) is a Maryland bipolar forceps, and the right instrument identification display 608b, 708b shows that the instrument controlled by the right gripping mechanism 122b (and thus the user's right hand) is a permanent cautery spatula. Of course, those having ordinary skill in the art would appreciate that those are just two exemplary surgical instrument types and the disclosure is not so limited. In addition, the GUI 600, 700 may include a left pedal auxiliary function indication 610a, 710a and a right pedal auxiliary function indication 610b, 710b, which each indicates the auxiliary functions assigned to the respective pedals, e.g., pedals 124a-124d, at a relative left-hand positioning and a relative right-hand positioning. Other pedals (not shown) also could be displayed and assigned differing auxiliary functions that could be conveyed to the user in a similar manner in accordance with the present disclosure.

Turning back to FIG. 5, and referring to the screen capture shown in FIG. 6, at operation 504, based on receipt of an indication signal from one or more processors of the control system at, for example, the surgeon console 120, the control cart 130, etc., an indication of the user's detected presence is displayed at the GUI 600. In the exemplary embodiment shown in FIG. 6, indication bar 606a illustrates an unhighlighted state, while indication bar 606b illustrates a highlighted state. The unhighlighted state at indication bar 606a of the illustrative example of FIG. 6 indicates that the user's presence is not detected in the immediate vicinity of any of the left bank of foot pedals 124a, 124b.

According to various exemplary embodiments, the user's detected presence is determined, by the control system, to be at, or above, a particular left bank or right bank of the foot pedals. By way of particular example, when a user's presence is detected above foot pedal 124c, which is located on the right bank of the foot pedals 124c, 124d, then the control system transmits a signal to the display indicating the auxiliary input devices at which the user presence is detected. A portion of the GUI 600 at which the indication is displayed corresponds to the left hand or right hand with which the foot pedal is mapped, e.g., foot pedal 124c at the right bank, at which the presence of the user has been detected. For example, the indication bar 606b at the right side 604 of the GUI 600 displays an indication of the corresponding position of the user's hand and the foot pedal 124c at the right bank of foot pedals. In this case, the indication bar 606b becomes highlighted (e.g., via a particular color) to indicate the detected presence and is different from the unhighlighted bar (and/or different color bar), which is illustrated at indication bar 606a.

Referring again to the exemplary workflow of FIG. 5, at operation 506, the actuation of one of the auxiliary function input devices, e.g., foot pedals 124a-124d, is detected by any of a variety of actuation detection devices provided at, or connected with, each of the foot pedals 124a-124d. When the actuation of one or more of the foot pedals 124a-124d occurs, the actuation detection device that detects the actuation of a particular foot pedal, e.g., foot pedal 124a, transmits an actuation detection signal indicating the actuation of the foot pedal. The actuation detection signal may be received at one or more processors located at, for example, the surgeon console 120, or may be transmitted to, for example, the core processor 150 at the control cart 130. The processors receive the actuation detection signal and output a signal to the display, such as display 126 or display 132. In one exemplary embodiment, the actuation detection occurs by switches associated with the pedals, as those skilled in the art would be familiar with.

Referring now to the screen capture shown in FIG. 7, at operation 508 of the workflow according to the exemplary embodiment of FIG. 5, an indication of the relative left or right handed mapped actuated input device, e.g., one of foot pedals 124a-124d, is displayed at the GUI 700. The displayed indication is displayed at, for example, the display 126 or 132, based on receipt of an indication signal from one or more processors of the control system at, for example, the surgeon console 120, the control cart 130, etc. In the exemplary embodiment shown in FIG. 7, indication bar 706a illustrates a highlighted state, while indication bar 706b illustrates an unhighlighted state. The unhighlighted state at indication bar 706b of the illustrative example of FIG. 7 indicates that none of the foot pedals 124c, 124d of the right bank of foot pedals is actuated.

According to various exemplary embodiments, the control system determines that one of the foot pedals 124a-124d mapped to control the auxiliary functions of instruments being controlled by a user's left- or right-hand has been actuated. For example, the system can detect that one of the pedals 124a, 124b of the left bank or the pedals 124c, 124d of the right bank has been actuated. When the foot pedal 124a, which is located on the left bank of the foot pedals, is actuated, then the control system transmits a signal to the display indicating the relative left hand or right hand mapping of the actuated auxiliary input device, e.g., foot pedal 124a. A portion of the GUI 700 at which the indication is displayed corresponds to the hand with which the actuated foot pedal is mapped. For example, the indication bar 706a at the left side 702 of the GUI 700 displays an indication of the actuated foot pedal 124a assigned to control the left hand mapped surgical instrument based on its left bank positioning. In this case, the indication bar 706a becomes highlighted a particular color (or includes some other indicator) indicative of the actuation and is different from both the unhighlighted bar, illustrated in FIG. 7 at indication bar 706b, and is also different from the highlighted bar which indicates a user's presence in the vicinity of one or more of the foot pedals illustrated in FIG. 6 at indication bar 606b.

Thus, according to various exemplary embodiments, an indication of a left hand or right hand mapped position of an auxiliary function input device, e.g., one of foot pedals 124a-124d, at which a user's presence is detected or which is actuated, is displayed to a user of the teleoperated surgical system 100 on a GUI. In this way, the GUI can immediately indicate to the user the left-hand or right-hand mapped auxiliary input device of both the particular proximally located auxiliary function input device (e.g., via the presence detection) or actuated auxiliary function input device.

Figure 8:
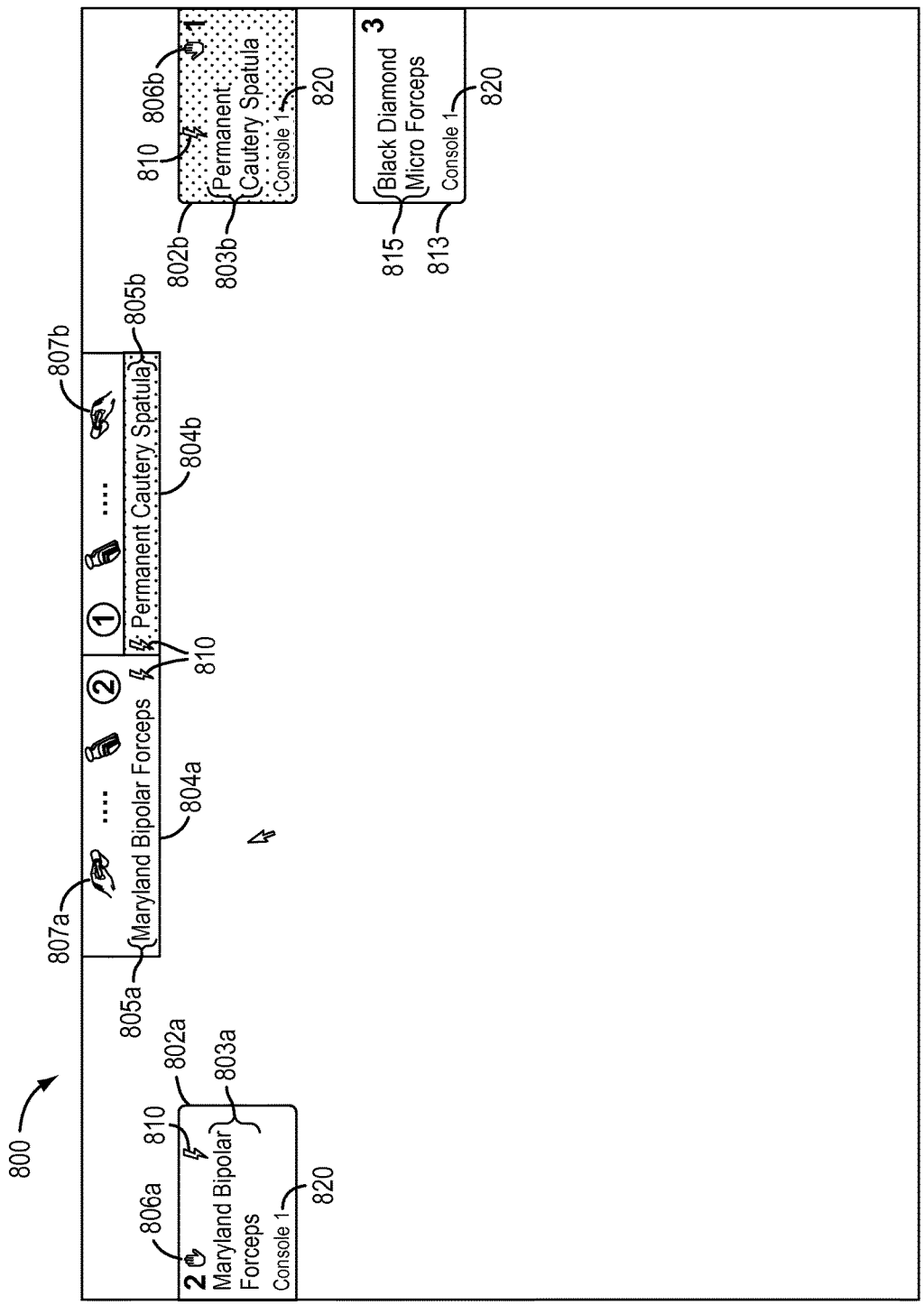
FIG. 8 is yet another exemplary screen of a graphical user interface in accordance with the present disclosure.
Figure 9:
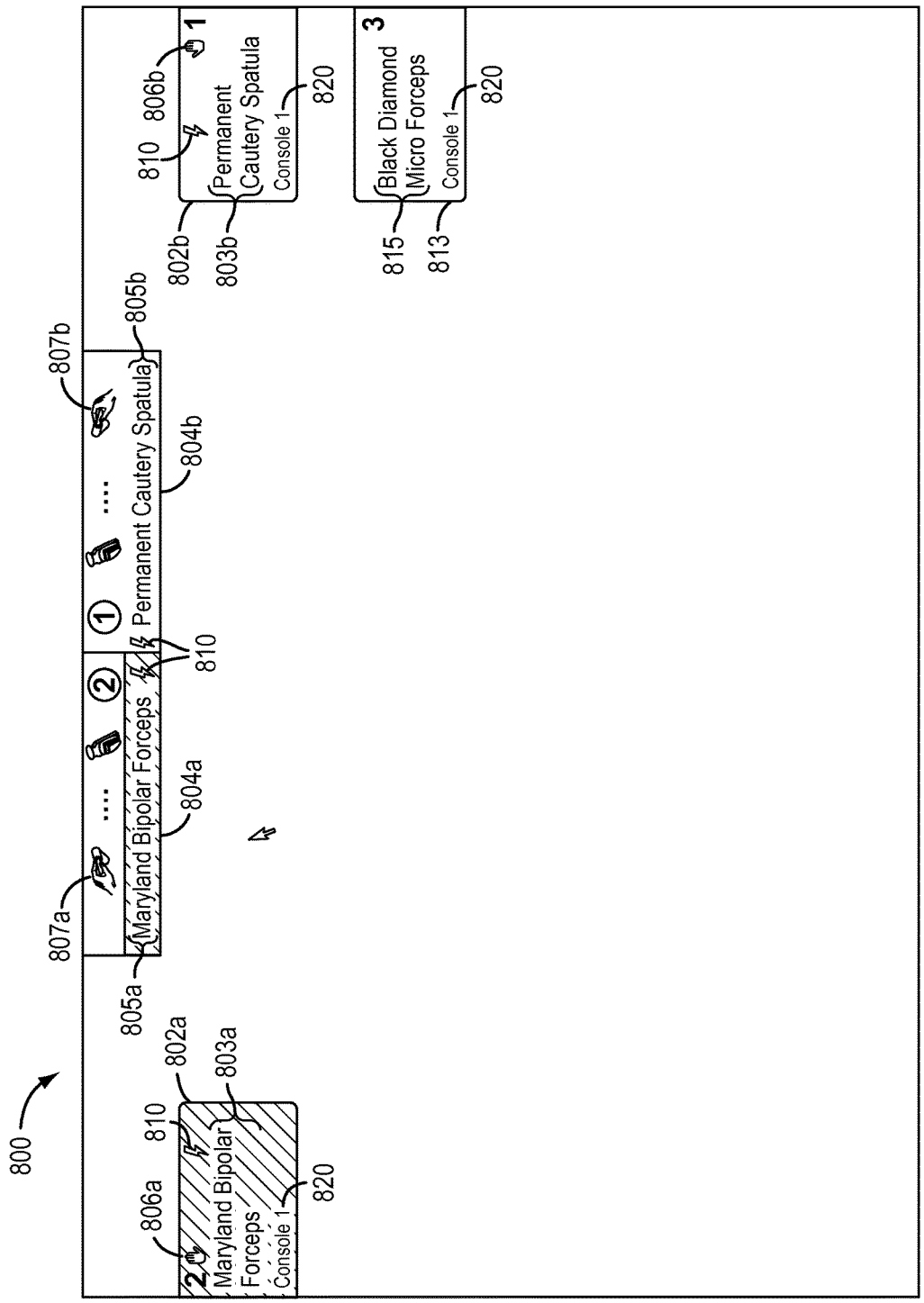
FIG. 9 is another exemplary screen of a graphical user interface in accordance with the present disclosure.

Various exemplary embodiments of the present disclosure include a graphical user interface for a patient side assistant's display, which may be located, for example, at the display 132 of control cart 130. Referring to FIGS. 8 and 9, one exemplary embodiment of a graphical user interface that may be useful to convey a variety of information regarding the teleoperated surgical system, and in particular useful to a patient side assistant, is depicted. As with FIGS. 6 and 7, the screen shot of FIGS. 8 and 9 does not illustrate various images that may be shown on the display along with the GUI components illustrated, such as the images delivered from an endoscopic imaging device and/or other GUI components.

In FIGS. 8 and 9, the surgical instrument that is in an in-following state with each of the user's left and right hands, respectively, is indicated generally by indication features 802a, 802b, located at the left and right sides of the screen, as well as by indication features 804a, 804b located at the upper portion of the screen to the left and right respectively of each other, with the left and right being from the perspective of an observer facing the screen. The indication features 802, 804 may include a left instrument identification display 803a, 805a and a right instrument identification display 803b, 805b which indicate to the user the type of instrument currently responsive to the master input devices that are controlled by the left and/or right hands, e.g., in-following with gripping mechanism 122a, 122b. One or more other indication features, such as indication feature 813, may also be displayed with an instrument identification display 815 to indicate that another surgical instrument is operably coupled to a manipulator interface assembly but is not in an in-following state under the control of a master input device. The instrument identification display 815 indicates of what type that surgical instrument is. In addition to indicating the type of surgical instrument, the indication features also can include information about which of a surgeon's console the instrument is assigned to be under the control of, which may be useful in dual or plural surgeon console settings. Thus, in FIGS. 8 and 9, each of the indication features 802, 804, 813 depict a console indication display at 820.

Corresponding to the examples shown in FIGS. 6 and 7, the left instrument identification displays 803a, 805a shows that the instrument controlled by the left gripping mechanism 122a (and thus the user's left hand) is a Maryland bipolar forceps, and the right instrument identification displays 803b, 805b shows that the instrument controlled by the right gripping mechanism 122b (and thus the user's right hand) is a permanent cautery spatula. Of course, those having ordinary skill in the art would appreciate that those are just two exemplary surgical instrument types and the disclosure is not so limited. In addition to the placement of these indication features 802, 804 at the left and right side of the screen, respectively, in various exemplary embodiments left hand icons 806a, 807a and right hand icons 806b, 807b may be displayed to provide an additional visual representation of which of the user's hands is in control of which in-following surgical instrument.

In various exemplary embodiments, the indication features 802, 804 also display an icon that indicates the surgical instrument is ready to execute an auxiliary function upon receiving a command from an auxiliary input device. By way of example, the screen shot of FIGS. 8 and 9 displays a lightning bolt icon 810 in each of the indication features 802, 804 indicating a readiness of the surgical instruments to execute an auxiliary function. The icon 810 is displayed when an instrument that is capable of performing an auxiliary function that is controlled by an auxiliary input device is operably coupled to a manipulator interface assembly that is under the control of a master input device (in-following). Those having ordinary skill in the art will appreciate that the lightning bolt is an exemplary icon that may be displayed to indicate a readiness of a surgical instrument to execute an auxiliary function and numerous other icons could be displayed to indicate such a state. Moreover, differing icons may be used, for example, depending on what auxiliary function the instrument performs; additionally, more than one such icon may be displayed at the same time, for example, to indicate that an instrument is in a ready state to perform more than one auxiliary function.

As with the graphical user interface described above with reference to FIGS. 6 and 7, the graphical user interface of FIGS. 8 and 9 in exemplary embodiments can indicate the user's detected presence in the proximity of (FIG. 8) or the actuation (firing) of (FIG. 9) an auxiliary input device that corresponds to the left or right hand-controlled instrument with which the auxiliary input device is mapped.

For example, in FIG. 8, the indication features 802, 804 can be highlighted a different color or otherwise altered, to convey to a user that a user's presence is detected in the proximity of either a right or left bank of auxiliary input devices. As shown in FIG. 8, for example, the shading to indicate highlighting or a differing color at 802b, 804b versus the unshaded features 802a, 804a, for example, may be displayed when a user's presence is detected in the proximity to any of the right bank of auxiliary input devices, e.g., foot pedals 124c, 124d. Thus, as depicted in FIG. 8, the indication features 802b, 804b can be differently highlighted (e.g., via a particular color) or otherwise altered to indicate which of the left hand and right hand controlled instruments a user may be about to actuate based on the presence detection in the proximity of a particular bank of auxiliary input devices.

Similarly, such altering of the indication features 802, 804 can be used to indicate that a particular auxiliary input device has been actuated to provide a command signal to activate the auxiliary function of a surgical instrument. FIG. 9 also is used as an exemplary way to indicate this with the shading at 802a, 804a at the left side of the GUI 900 in order to display an indication of the actuated auxiliary input device, e.g., one of foot pedals 124a, 124b assigned to control the left hand mapped surgical instrument based on its left bank positioning. In an exemplary embodiment, as depicted by the differing shading utilized in FIGS. 8 and 9, the highlighting, colors, or other indications are different to indicate the presence detection versus the activation.

Those having ordinary skill in the art would appreciate that various modifications could be made to the GUI screens depicted in the exemplary embodiments of FIGS. 6-9, while conveying similar information to user(s) of a teleoperated surgical system and without departing from the scope of the present teachings. For example, differing kinds and combinations of icons and/or text may be employed to convey the information discussed above, flashing or other indicators could be used in lieu of or in combination with colors or highlighting of indication features, and/or differing placement of particular features of the screen shot may also be used to some extent without departing from the scope of the present disclosure.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A method of assigning an auxiliary input device to control a surgical instrument in a robotic surgical system, the method comprising:

detecting a first surgical instrument coupled to a first manipulator interface assembly of a teleoperated surgical system, the first manipulator interface assembly being controlled by a first input device;

detecting which one of a user's left hand and right hand operates the first input device; and assigning control of an auxiliary function of the first surgical instrument to a first auxiliary input device disposed in a left position relative to a second auxiliary input device if the user's left hand is detected to operate the first input device, or assigning control of an auxiliary function of the first surgical instrument to the second auxiliary input device disposed in a right position relative to the first auxiliary input device if the user's right hand is detected to operate the first input device, wherein a frame of reference of the left position and right position is relative to a user operating the first input device.

2. The method of claim 1, wherein the auxiliary function comprises an electrosurgical function.

3. The method of claim 1, wherein the first input device comprises a gripping mechanism.

4. The method of claim 1, further comprising
detecting a second surgical instrument coupled to a second manipulator interface assembly of the teleoperated surgical system, the second manipulator interface assembly being controlled by a second input device;
detecting which one of the user's left hand and right hand operates the second input device; and
assigning control of an auxiliary function of the second surgical instrument to the second auxiliary input device if the user's left hand is detected to operate the second input device, or
assigning control of the auxiliary function of the second surgical instrument to the second auxiliary input device if the user's right hand is detected to operate the second input device.

5. A method for controlling a surgical instrument in a computer-assisted surgical system, the method comprising:
receiving at a controller a signal indicative of a surgical instrument being in an in-following status with a first input device positioned to receive input from one of a user's right or left hands;
detecting a change in the in-following status of the surgical instrument from the first input device to a second input device positioned to receive input from the other of the user's right hand and left hand; and
automatically re-assigning control of an auxiliary function of the surgical instrument from a first auxiliary input device to a second auxiliary input device based on detecting the change of the in-following status.

6. The method of claim 5, wherein the first auxiliary input device and the second auxiliary input device have relative left and right positioning with respect to each other.

7. The method of claim 5, wherein control of the auxiliary function of the surgical instrument is automatically re-assigned from the first auxiliary input device to the second auxiliary input device during a surgical procedure.

8. The method of claim 5, wherein an original assignment of auxiliary functions are automatically re-assigned during a procedure based on detecting the change of the in-following status of the first and second input devices.

9. The method of claim 5, further comprising:
after automatically re-assigning control of the auxiliary function of the surgical instrument from the first auxiliary input device to the second auxiliary input device, activating the auxiliary function of the surgical instrument in response to an input command signal received from the second auxiliary input device.

10. The method of claim 5, wherein the auxiliary function is chosen from at least one of delivering energy, image and/or audio streaming, irrigation, suction, stapling, and cutting.

11. The method of claim 5, further comprising:
detecting actuation of the second auxiliary input device or a presence of a user in proximity to the second auxiliary input device; and
in response to the detecting the presence, displaying an indication at a portion of a graphical user interface indicating the surgical instrument to which the second auxiliary input device is assigned control.

12. The method of claim 5, further comprising:
detecting an auxiliary function type of the surgical instrument; and
sending a signal from the first or second auxiliary input device to activate the auxiliary function of the surgical instrument based on detecting of the auxiliary function type and of the in-following status of the surgical instrument.

13. The method of claim 1, further comprising:
activating the auxiliary function of the surgical instrument in response to input at the assigned one of the first auxiliary input device and second auxiliary input device.

14. The method of claim 1, wherein the auxiliary function is chosen from at least one of delivering energy, image and/or audio streaming, irrigation, suction, stapling, and cutting.

15. The method of claim 1, further comprising:
detecting actuation of the first auxiliary input device or a presence of a user in proximity to the first auxiliary input device; and
in response to the detecting the actuation or presence, displaying an indication at a portion of a graphical user interface indicating the surgical instrument to which the first auxiliary input device is assigned control.

16. A system for controlling a surgical instrument, the system comprising:
a first input device operably coupled to generate and transmit a first input control signal to remotely control movement of a surgical instrument operably coupled to a computer-assisted surgical system;
a second input device operably coupled to generate and transmit a second input control signal to remotely control movement of a surgical instrument operably coupled to a computer-assisted surgical system
a first auxiliary input device configured to transmit a first auxiliary function control signal to activate an auxiliary function of a surgical instrument in an operably coupled state of the first auxiliary input device and the surgical instrument;
a second auxiliary input device configured to transmit a second auxiliary function control signal to activate an auxiliary function of a surgical instrument in an operably coupled state of the second auxiliary input device and the surgical instrument; and
a control system configured to:
detect change with regard to which of the first and second input devices the surgical instrument is in an in-following status with; and
selectively assign control of the auxiliary function of the surgical instrument to the first or second auxiliary input devices based on detecting the change of the in-following status.

17. The system of claim 16, wherein the first input device and the second input device comprise gripping mechanisms.

18. The system of claim 16, further comprising a readable memory structure associated with the surgical instrument, the control system being further configured to receive data from the readable memory structure identifying the auxiliary function type of the surgical instrument.

19. The system of claim 16, further comprising:
   a graphical user interface configured to provide an indication of a detected presence of the user in proximity to the first or second auxiliary input devices.

20. The system of claim 16, wherein the first and second auxiliary input devices comprise foot pedals.

* * * * *